(12) United States Patent
Choi

(10) Patent No.: US 10,799,207 B2
(45) Date of Patent: Oct. 13, 2020

(54) ULTRASOUND IMAGING APPARATUS AND CONTROL METHOD FOR THE SAME

(71) Applicant: SAMSUNG MEDISON CO., LTD., Gangwon-do (KR)

(72) Inventor: Sung-Jin Choi, Seoul (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 647 days.

(21) Appl. No.: 15/378,979

(22) Filed: Dec. 14, 2016

(65) Prior Publication Data
US 2017/0196532 A1    Jul. 13, 2017

(30) Foreign Application Priority Data
Jan. 12, 2016    (KR) .......................... 10-2016-0003484

(51) Int. Cl.
A61B 8/00    (2006.01)
A61B 8/08    (2006.01)
(Continued)

(52) U.S. Cl.
CPC .............. *A61B 8/00* (2013.01); *A61B 8/4405* (2013.01); *A61B 8/4416* (2013.01);
(Continued)

(58) Field of Classification Search
USPC .......................................................... 367/7
See application file for complete search history.

(56) References Cited

U.S. PATENT DOCUMENTS 8,427,537 B2 *   4/2013   Rouzes .................... G06T 7/73
                                                    348/140
9,632,580 B2 *   4/2017   Kim ....................... G06F 3/013
(Continued)

FOREIGN PATENT DOCUMENTS

EP      2804147 A2      11/2014
JP      2009-112468 A    5/2009
KR      20160014933 A *  2/2016   ............. G06F 3/013

OTHER PUBLICATIONS

Extended European Search Report dated May 30, 2017 issued in European Patent Application No. 16171728.5.
(Continued)

*Primary Examiner* — James R Hulka
(74) *Attorney, Agent, or Firm* — Morgan Lewis & Bockius LLP

(57) ABSTRACT

Disclosed herein are an ultrasound imaging apparatus and a control method thereof. The ultrasound imaging apparatus includes: a display unit configured to display an ultrasound image and an external image such that a first reference line overlaps the ultrasound image and a second reference line overlaps the external image; an ultrasound probe configured to receive a command for moving or rotating at least one image of the ultrasound image and the external image based on a predetermined reference coordinate system; and a controller configured to determine whether the ultrasound image matches with the external image according to manipulation of the ultrasound probe, and to control the display unit to synthesize the ultrasound image with the external image and to display the ultrasound image and the external image, if determining that the ultrasound image matches with the external image.

28 Claims, 15 Drawing Sheets

(51) Int. Cl.
*G01S 7/52* (2006.01)
*G01S 15/42* (2006.01)

(52) U.S. Cl.
CPC ............ *A61B 8/4427* (2013.01); *A61B 8/463* (2013.01); *A61B 8/465* (2013.01); *A61B 8/467* (2013.01); *A61B 8/5261* (2013.01); *G01S 7/52053* (2013.01); *G01S 7/52087* (2013.01); *G01S 15/42* (2013.01); *A61B 8/0866* (2013.01); *A61B 8/4254* (2013.01); *A61B 8/4472* (2013.01); *A61B 8/4488* (2013.01)

(56) References Cited

U.S. PATENT DOCUMENTS

| | | | |
|---|---|---|---|
| 2009/0074267 A1* | 3/2009 | Pedrizzetti | A61B 5/055 382/128 |
| 2009/0097778 A1 | 4/2009 | Washburn et al. | |
| 2010/0298704 A1* | 11/2010 | Pelissier | A61B 8/0833 600/443 |
| 2010/0298705 A1* | 11/2010 | Pelissier | A61B 8/0833 600/443 |
| 2010/0331693 A1* | 12/2010 | Matsunaga | A61B 8/02 600/443 |
| 2013/0102865 A1* | 4/2013 | Mandelis | A61B 5/0095 600/328 |
| 2014/0276059 A1 | 9/2014 | Sheehan | |
| 2015/0105658 A1 | 4/2015 | Park et al. | |
| 2016/0034031 A1* | 2/2016 | Kim | G06F 3/013 345/629 |
| 2016/0252325 A1* | 9/2016 | Sammut | F41G 1/38 42/122 |

OTHER PUBLICATIONS

Communication Pursuant to Article 94(3) EPC from the European Patent Office issued in related European Application No. 16 171 728.5 dated Jan. 29, 2019.

* cited by examiner

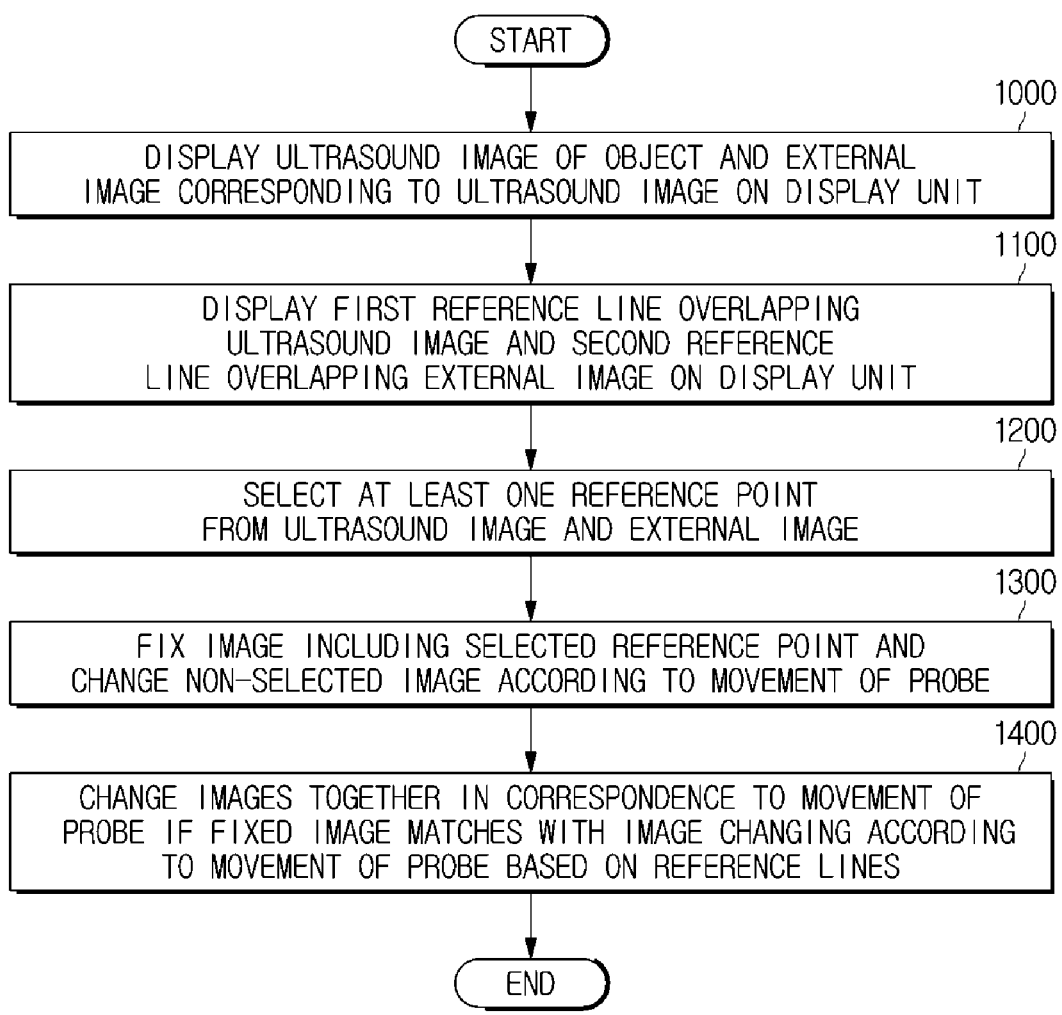

FIG. 8
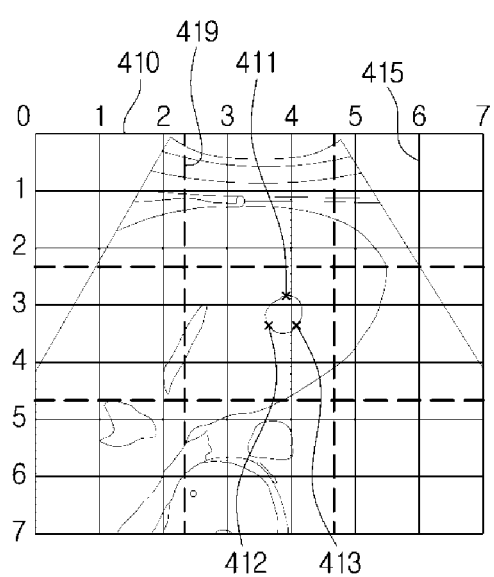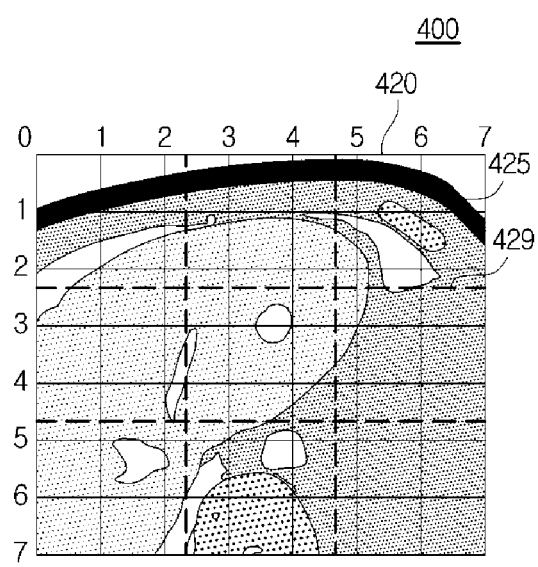

FIG. 11

| IMAGE ROTATED WITH RESPECT TO X-AXIS | IMAGE ROTATED WITH RESPECT TO Y-AXIS | IMAGE ROTATED WITH RESPECT TO Z-AXIS |
|---|---|---|
| c1 | c4 | c7 |
| c2 | c5 | c8 |
| c3 | c6 | c9 |

ULTRASOUND IMAGING APPARATUS AND CONTROL METHOD FOR THE SAME

CROSS-REFERENCE TO RELATED APPLICATION

This application claims the benefit of Korean Patent Application No. 10-2016-0003484, filed on Jan. 12, 2016 in the Korean Intellectual Property Office, the disclosure of which is incorporated herein by reference.

BACKGROUND

1. Field

Embodiments of the present disclosure relate to an ultrasound imaging apparatus and a control method thereof.

2. Description of the Related Art

An ultrasound imaging apparatus irradiates ultrasonic waves onto the surface of an object toward a specific part of the object, and receives echo ultrasonic waves reflected from the specific part of the object so as to non-invasively acquire slice images about the soft tissues of the object or images about blood vessels of the object based on information of the echo ultrasonic waves.

The ultrasound imaging apparatus has advantages that it is a compact, low-priced apparatus and it can display images in real time. Also, the ultrasound imaging apparatus has high safety since there is no risk for patients to be exposed to radiation such as X-rays. For the advantages, the ultrasound imaging apparatus is widely used to diagnose the heart, breasts, abdomen, urinary organs, uterus, etc.

Lately, studies into an ultrasound imaging apparatus of registering an external image of an object acquired through an external imaging apparatus with an ultrasound image to provide the registered images to a user are actively conducted. The ultrasound imaging apparatus registers an external image of an object, such as a Computerized Tomography (CT) image and a Magnetic Resonance (MR) image, with an ultrasound image to display the registered images through a display.

SUMMARY

Therefore, it is an aspect of the present disclosure to provide an ultrasound imaging apparatus of matching, when displaying an ultrasound image and an external image registered with the ultrasound image on a display unit, the ultrasound image with the external image based on reference lines displayed on the display unit, using a ultrasound probe, to provide more accurately and precisely re-registered images, and a method of controlling the ultrasound imaging apparatus.

It is another aspect of the present disclosure to provide an ultrasound imaging apparatus of fixing one of two images, comparing the fixed image to the other image changing in correspondence to movement of an ultrasound probe, using the ultrasound probe, and then synchronizing and displaying the two images, in order to match the two images based on reference lines output on a display unit to obtain more accurately and precisely re-registered images, and a method of controlling the ultrasound imaging apparatus.

Additional aspects of the disclosure will be set forth in part in the description which follows and, in part, will be obvious from the description, or may be learned by practice of the disclosure.

In accordance with one aspect of the present disclosure, an ultrasound imaging apparatus including: a display unit configured to display an ultrasound image and an external image such that a first reference line overlaps the ultrasound image and a second reference line overlaps the external image; an ultrasound probe configured to receive a command for moving or rotating at least one image of the ultrasound image and the external image based on a predetermined reference coordinate system; and a controller configured to determine whether the ultrasound image matches with the external image according to manipulation of the ultrasound probe, and to control the display unit to synthesize the ultrasound image with the external image and to display the ultrasound image and the external image, if determining that the ultrasound image matches with the external image.

If a command for selecting a first reference point of the ultrasound image is input by a user, the controller may fix the ultrasound image including the first reference point, and control the display unit to change the external image in correspondence to movement of the ultrasound probe.

The controller may determine whether the fixed ultrasound image matches with the external image changing in correspondence to movement of the ultrasound probe adjusted by the user, based on the first reference line displayed on the ultrasound image and the second reference line displayed on the external image, and control the display unit to synchronize the ultrasound image with the external image and to display the ultrasound image and the external image, if determining that the ultrasound image matches with the external image.

If a command for selecting a second reference point of the external image is input by a user, the controller may fix the external image including the second reference point, and control the display unit to change the ultrasound image in correspondence to movement of the ultrasound probe.

The controller may determine whether the fixed external image matches with the ultrasound image changing in correspondence to movement of the ultrasound probe adjusted by the user, based on the first reference line displayed on the ultrasound image and the second reference line displayed on the external image, and control the display unit to synchronize the ultrasound image with the external image and to display the ultrasound image and the external image, if determining that the external image matches with the ultrasound image.

The display unit may display the first reference line and the second reference line in the form of grids formed with at least one line of a straight line and a curved line.

The display unit may further display at least one of a character, a symbol, a numeral, and a figure around the first reference line and the second reference line, or at an intersection of the first reference line and the second reference line.

The first reference line and the second reference line may be displayed with the same color or with different colors according to a brightness of the entire or a part of the ultrasound image or a brightness of the entire or a part of the external image.

The controller may register the ultrasound image with the external image.

The display unit may display the ultrasound image and the external image registered with the ultrasound image.

The display unit may display a first reference point of the ultrasound image or a second reference point of the external image, as at least one of a character, a symbol, a numeral, and a figure that is displayed in at least one position.

The ultrasound probe may include at least one sensor of a position sensor, an accelerometer, a magnetic sensor, and a gyro sensor.

The ultrasound probe may receive a command for moving or rotating at least one image of the ultrasound image and the external image based on the predetermined reference coordinate system, through the at least one sensor.

The controller may acquire information about a position and a direction of an object, using the ultrasound probe.

The external image may include at least one image of a re-sliced Computed Tomography (CT) image and a Magnetic Resonance Imaging (MRI), corresponding to the ultrasound image.

The predetermined reference coordinate system may be formed with an x-axis, a y-axis, and a z-axis.

In accordance with another aspect of the present disclosure, a method of controlling an ultrasound imaging apparatus including: displaying an ultrasound image and an external image such that a first reference line overlaps the ultrasound image and a second reference line overlaps the external image; receiving a command for moving or rotating at least one image of the ultrasound image and the external image based on a predetermined reference coordinate system; and determining whether the ultrasound image matches with the external image according to manipulation of the ultrasound probe, and controlling a display unit to synthesize the ultrasound image with the external image and to display the ultrasound image and the external image, if it is determined that the ultrasound image matches with the external image.

The controlling of the display unit may include: receiving a command for selecting a first reference point of the ultrasound image from a user; fixing the ultrasound image including the first reference point; and controlling the display unit to change the external image in correspondence to movement of the ultrasound probe.

The controlling of the display unit may include: determining whether the fixed ultrasound image matches with the external image changing in correspondence to movement of the ultrasound probe adjusted by the user, based on the first reference line displayed on the ultrasound image and the second reference line displayed on the external image; and controlling the display unit to synchronize the ultrasound image with the external image and to display the ultrasound image and the external image, if it is determined that the ultrasound image matches with the external image.

The controlling of the display unit may include: receiving a command for selecting a second reference point of the external image from a user; fixing the external image including the second reference point; and controlling the display unit to change the ultrasound image in correspondence to movement of the ultrasound probe.

The controlling of the display unit may include: determining whether the fixed external image matches with the ultrasound image changing in correspondence to movement of the ultrasound probe adjusted by the user, based on the first reference line displayed on the ultrasound image and the second reference line displayed on the external image; and controlling the display unit to synchronize the ultrasound image with the external image and to display the ultrasound image and the external image, if it is determined that the external image matches with the ultrasound image.

The displaying of the ultrasound image and the external image may include displaying the first reference line and the second reference line in the form of grids formed with at least one line of a straight line and a curved line.

The displaying of the ultrasound image and the external image may include further displaying at least one of a character, a symbol, a numeral, and a figure around the first reference line and the second reference line, or at an intersection of the first reference line and the second reference line.

The first reference line and the second reference line may be displayed with the same color or with different colors according to a brightness of the entire or a part of the ultrasound image or a brightness of the entire or a part of the external image.

The controlling of the display unit may include registering the ultrasound image with the external image.

The displaying of the ultrasound image and the external image may include displaying the ultrasound image and the external image registered with the ultrasound image.

The displaying of the ultrasound image and the external image may include displaying a first reference point of the ultrasound image or a second reference point of the external image, as at least one of a character, a symbol, a numeral, and a figure that is displayed in at least one position.

The ultrasound probe may include at least one sensor of a position sensor, an accelerometer, a magnetic sensor, and a gyro sensor.

The ultrasound probe may receive a command for moving or rotating at least one image of the ultrasound image and the external image based on the predetermined reference coordinate system, through the at least one sensor.

The controlling of the display unit may include acquiring information about a position and a direction of an object, using the ultrasound probe.

The external image may include at least one image of a re-sliced Computed Tomography (CT) image and a Magnetic Resonance Imaging (MRI), corresponding to the ultrasound image.

The predetermined reference coordinate system may be formed with an x-axis, a y-axis, and a z-axis.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 6 is a flowchart illustrating a method of accurately and quickly re-registering an ultrasound image with an external image registered with the ultrasound image on a display unit according to an embodiment of the present disclosure;

FIG. 8 shows reference lines displayed on a display unit according to an embodiment of the present disclosure, and other reference lines changing in correspondence to movement of an ultrasound probe;

FIG. 11 relates to examples of showing rotation of an image according to movement of an ultrasound probe according to an embodiment of the present disclosure, using dotted reference lines;

DETAILED DESCRIPTION

Figure 1:
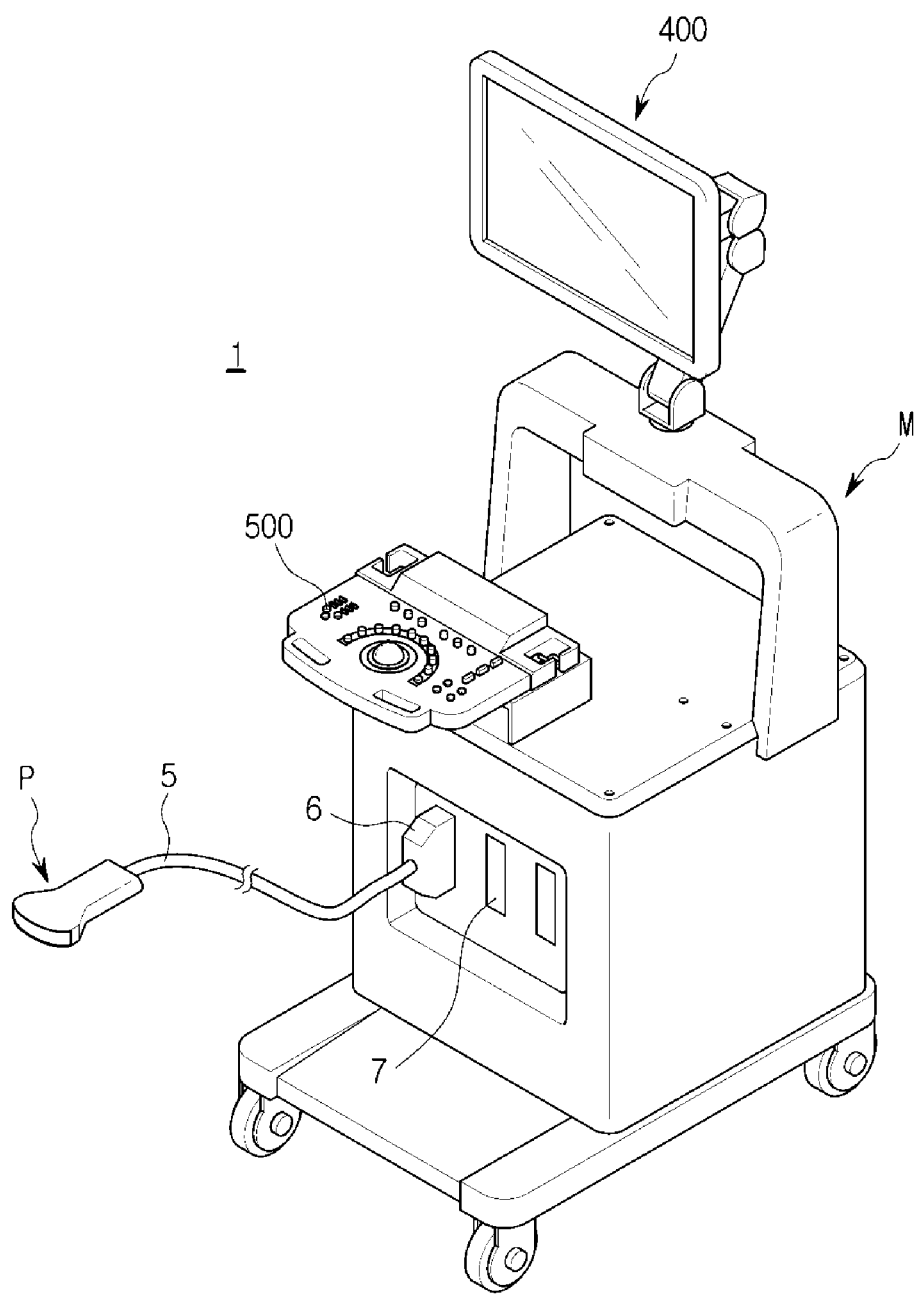
FIG. 1 is a perspective view of an ultrasound imaging apparatus according to an embodiment of the present disclosure.

Advantages and features of the present disclosure and a method of achieving the advantages and features will be apparent by referring to embodiments described below in connection with the accompanying drawings.

Configurations illustrated in the embodiments and the drawings described in the present specification are only the preferred embodiments of the present disclosure, and thus it is to be understood that various modified examples, which may replace the embodiments and the drawings described in the present specification, are possible when filing the present application. Also, throughout the drawings, like reference numerals will be understood to refer to like components.

In this specification, it will be understood that the case in which a certain part is "connected" to another part includes the case in which the part is "electrically connected" to the other part with another device in between, as well as the case in which the part is "directly connected" to the other part. Also, it will be understood that when a certain part "includes" a certain component, the part does not exclude another component but can further include another component, unless the context clearly dictates otherwise.

In this specification, an "object" means a human body, an animal, or a part of a human body or an animal. For example, the object may include vessels or organs, such as a liver, a heart, a uterus, a brain, breasts, abdomen, etc. Also, in this specification, a "user" may be a medical professional, such as a doctor, a nurse, a medical technologist, or a medical imaging professional, or may be a technician that repairs medical equipment, although not limited to them.

In this specification, an "ultrasound image" means an image of an object acquired using ultrasonic waves. Also, in this specification, an "external image" means an image of an object acquired using medical equipment, such as an X-ray diagnosis apparatus, a Computerized Tomography (CT) scanner, a Magnetic Resonance Imaging (MRI) apparatus, and a nuclear medical diagnostic apparatus. Also, the "external image" may mean a CT image, a Magnetic Resonance (MR) image, a 3Dimensional (3D) volume CT image, a 3D volume MR image, and a planar image sliced from one of the images, corresponding to an ultrasound image of an object acquired using an ultrasound probe. Also, a diagnosis apparatus which the ultrasound imaging apparatus and the control method for the same according to embodiments of the present disclosure can be applied to or used in may be one of an X-ray imaging apparatus, X-ray fluoroscopy equipment, a CT scanner, a MRI apparatus, a Positron Emission Tomography (PET) scanner, and an ultrasound imaging apparatus. In the following description, an ultrasound imaging apparatus is used as the diagnosis apparatus, however, the present disclosure is not limited to the ultrasound imaging apparatus.

Also, in this specification, it will be understood that when a certain part "includes" a certain component, the part does not exclude another component but can further include another component unless the context clearly dictates otherwise. Also, the term "part", "module", and the like mentioned in this specification mean a unit of processing at least one function or operation, and may be implemented as hardware, software, or a combination of hardware and software.

Hereinafter, embodiments of an ultrasound imaging apparatus and a control method for the same will be described with reference to FIGS. 1 to 12.

FIG. 1 is a perspective view of an ultrasound imaging apparatus according to an embodiment of the present disclosure.

As shown in FIG. 1, an ultrasound imaging apparatus 1 may include an ultrasound probe P, a main body M, a receiver connected to the main body M, a display unit 400, and an input unit 500.

Meanwhile, at the bottom of the main body M, a plurality of castors (not shown) may be provided to move the ultrasound imaging apparatus 1. The plurality of castors may fix the ultrasound imaging apparatus 1 at a specific location or move the ultrasound imaging apparatus 1 in a specific direction. The ultrasound imaging apparatus 1 is called a cart-type ultrasound imaging apparatus.

However, the ultrasound imaging apparatus 1 may be a portable ultrasound imaging apparatus that can be possessed by a user even when he/she moves to a long distance. The portable ultrasound imaging apparatus may include no castors. Examples of such a portable ultrasound imaging apparatus include a Picture Archiving and Communication System (PACS) viewer, a smart phone, a laptop computer, Personal Digital Assistant (PDA), and a tablet PC, although not limited to these.

The ultrasound probe P may contact the surface of an object to transmit/receive ultrasonic waves to/from the object. More specifically, the ultrasound probe P may include a plurality of transducer elements to convert electrical signals into ultrasonic signals and vice versa.

The plurality of transducer elements may be arranged on one surface of the ultrasound probe P. An ultrasound probe in which a plurality of transducer elements are arranged one-dimensionally on one surface is called a 1D array probe. The 1D array probe may include a linear array probe in which a plurality of transducer elements are arranged linearly, a phased array probe, and a convex array probe in which a plurality of transducer elements are arranged in a curved shape.

Unlike this, an ultrasound probe in which a plurality of transducer elements are arranged two-dimensionally is called a 2D array probe. In the 2D array probe, the plurality of transducer elements may be arranged on one plane. Alternatively, on one surface of the 2D array probe, the plurality of transducer elements may be arranged in a curved shape.

The transducer elements may vibrate according to a transmission signal received from the main body M to generate ultrasonic waves. The generated ultrasonic waves may be irradiated to the inside of the object. Also, the transducer elements may vibrate by echo ultrasonic waves reflected from a specific part inside the object to generate a reception signal corresponding to the echo ultrasonic waves. The reception signal may be transferred to the main body M to be used to create an ultrasound image.

In the following description, the transmission signal received by the ultrasound probe P will be referred to as an ultrasonic signal, and the reception signal generated by the ultrasound probe P will be referred to as an ultrasonic echo signal.

The ultrasound probe P may collect echo ultrasonic waves in real time to generate an ultrasonic echo signal with regular time intervals. The ultrasonic echo signal generated with time intervals may be used to create a frame image of an ultrasound image.

The ultrasound probe P may communicate with the main body M through a cable 5. For this, one end of the cable 5 may be connected to the ultrasound probe P, and a male connector 6 may be physically coupled with the other end of the cable 5. The male connector 6 connected to the other end of the cable 5 may be physically coupled with a female connector 7 of the main body M so that the ultrasound probe P can be connected to the main body M.

The ultrasound probe P may receive an ultrasonic signal from the main body M through the cable 5, or transmit an ultrasonic echo signal to the main body M. Also, the ultrasound probe P may receive a control signal from the main body M through the cable 5 to thereby be controlled by the main body M.

More specifically, if a control signal corresponding to a control command input through the input unit 500 is generated by the main body M, the ultrasound probe P may receive a control signal through the cable 5 to thereby be controlled according to the control signal. For example, if a control command for setting a focal depth of ultrasonic waves to be irradiated, the size or shape of aperture of the ultrasound probe P, a steering angle, etc. is input through the input unit 540, the main body M may generate a control signal corresponding to the control command. The generated control signal may be transferred to the ultrasound probe P through the cable 5 and used for beamforming.

Also, unlike the structure shown in FIG. 1, the ultrasound probe P may be connected to the main body M in a wireless fashion. In this case, the ultrasound probe P may receive an ultrasonic signal for irradiating ultrasonic waves from the main body M in a wireless fashion, or may transmit an ultrasonic echo signal corresponding to echo ultrasonic waves received from an object ob to the main body M in a wireless fashion.

The ultrasound probe P may adopt one of well-known wireless communication methods to be connected to the main body M. For example, the ultrasound probe P may be connected to the main body M through a wireless Internet, such as Wireless Local Area Network (WLAN), Wireless Fidelity (WiFi), Wireless Broadband (Wibro), World Interoperability for Microwave Access (Wimax), and High Speed Downlink Packet Access (HSDPA), or through a short-range communication method, such as Bluetooth, Radio Frequency Identification (RFID), Infrared Data Association (IrDA), Ultra Wideband (UWB), and Zigbee.

The display unit 400 may provide an ultrasound image of an object ob acquired by the ultrasound probe P or an external image received from an external medical apparatus to a user. Also, the display unit 400 may display an ultrasound image of an object and an external image registered with the ultrasound image through separate display panels, or may overlap the ultrasound image with the external image on a display panel.

The display unit 400 may be configured with one or more display panels. If the display unit 400 is configured with a plurality of display panels, the display unit may display different images on the respective display panels. Accordingly, the display unit 400 may display an ultrasound image acquired during ultrasonic diagnosis on one display panel, and display an external image acquired by another medical apparatus on another display panel.

The display unit 400 may be one of various well-known displays, such as a Cathode Ray Tube (CRT) and a Liquid Crystal Display (LCD). Also, the display unit 400 may provide 3D images as well as 2D images. Also, the display unit 400 may display various User Interfaces (UIs) related to the control of the ultrasound imaging apparatus 1. The user may view an UI provided through the display unit 400, and input a control command for controlling the ultrasound imaging apparatus 1 or a component of the ultrasound imaging apparatus 1 through the input unit 500.

The user may touch the display unit 400 to input a control command for controlling the ultrasound imaging apparatus 1 or to input a touch input command for setting an area of interest which the user will observe and diagnose from an ultrasound image of an object. The display unit 400 may include a touch panel capable of receiving a user's touch inputs. The touch panel may be a Liquid Crystal Display (LCD) panel, a Light Emitting Diode (LED) panel, or an Organic Light Emitting Diode (OLED) panel.

The input unit 500 may be configured to receive commands related to operations of the ultrasound imaging apparatus 1. The user may input various commands, such as a diagnosis start command, a target area selection command, a kind-of-diagnosis selection command, and a mode selection command for selecting a mode for an ultrasound image to be finally output, through the input unit 150. Also, the user may input a control command for registering an external image through the input unit 500. Also, the user may input a control command for setting a reference point for registering an ultrasound image with an external image, through the input unit 500. Also, the user may input a control command for fixing an external image or an ultrasound image displayed in correspondence to movement of the ultrasound probe, through the input unit 500. Also, the user may input a control command for displaying straight lines (hereinafter, referred to as "reference lines") for more accurately matching an ultrasound image with an external image registered with the ultrasound image on the display unit 400, through the input unit 500. Also, the user may input a control command for displaying characters, symbols, numerals, and figures around the reference lines, at the intersections of the reference lines, and at a reference point, through the input unit 500. Also, the user may input a control command for re-registering an ultrasound image with an external image, through the input unit 500.

According to an embodiment, the input unit 500 may be mounted on the main body M, as shown in FIG. 1. The input unit 500 may include at least one of a switch, a key, a wheel, a joystick, a trackball, and a knop. Also, if the display unit 400 is a touchable display panel, the display unit 400 may also function as an input unit. For example, the user may input a control command for controlling the ultrasound imaging apparatus 1 by touching the display panel.

Figure 2:
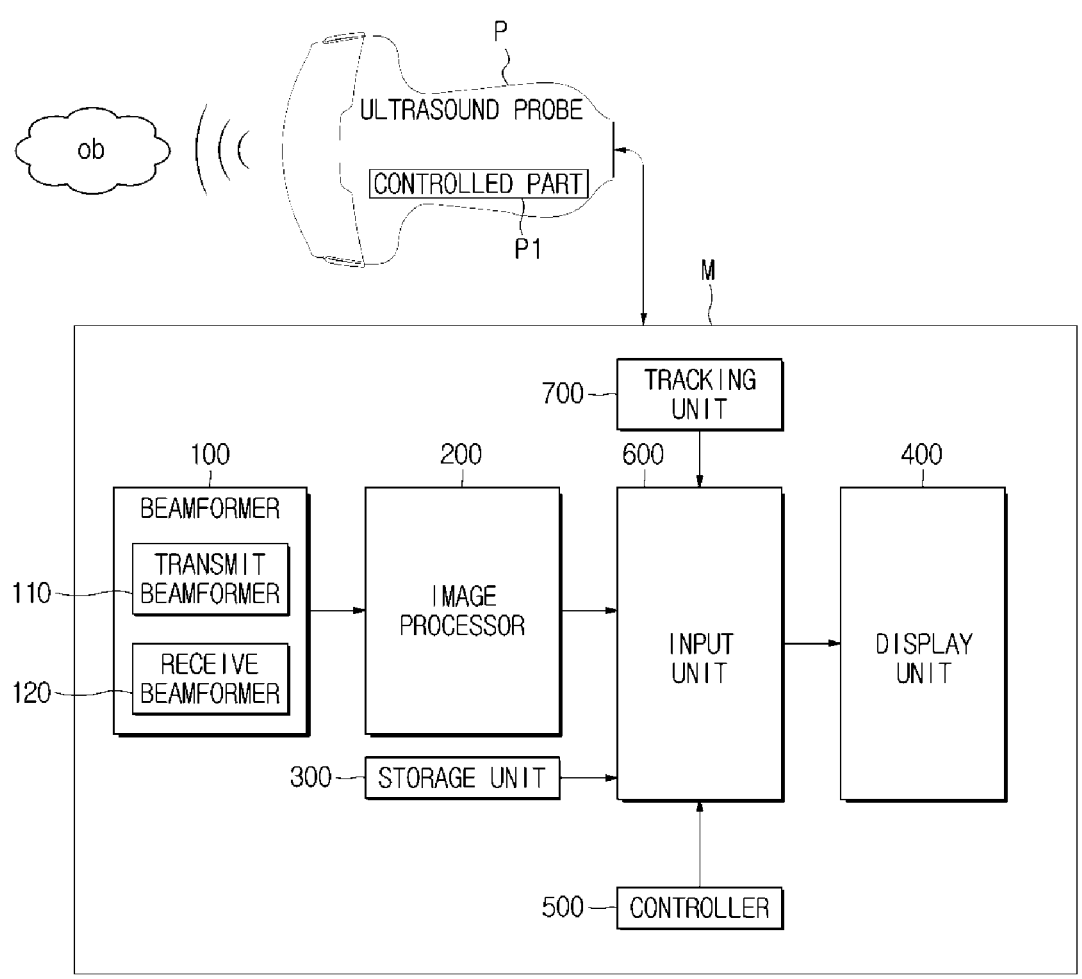
FIG. 2 is a control block diagram of an ultrasound imaging apparatus according to an embodiment of the present disclosure.

FIG. 2 is a control block diagram of the ultrasound imaging apparatus 1 according to an embodiment of the present disclosure.

The ultrasound imaging apparatus 1 may include the ultrasound probe P and the main body M.

The ultrasound probe P may include a controlled part P1. The ultrasound probe P may acquire information about its own location and direction through the controlled part P1.

More specifically, the controlled part P1 may include at least one sensor among a position sensor, an accelerometer, a magnetic sensor, and a gyro sensor. The controlled part P1 may use at least one sensor among the above-mentioned sensors to acquire information about the position and direction of the ultrasound probe P based on an initial position. More specifically, the initial position may be a point at which an object is first sensed by the ultrasound probe P, and the controlled part P1 may sense a position to which the ultrasound probe P moves or a direction in which the ultrasound probe P moves, based on the initial position, to acquire information about the position and direction of the ultrasound probe P. Also, the controlled part P1 may transfer the information about the position and direction of the ultrasound probe P, in the form of an electrical signal, to a tracking unit 700.

The tracking unit 700, which will be described later, may track a position of the ultrasound probe P, based on the information about the position and direction of the ultrasound probe P acquired by the controlled part P1. Also, the controlled part P1 may be tracked by electro-magnetic waves or light generated by the tracking unit 700 of the main body M.

The ultrasound probe P may receive a command for moving or rotating at least one of an ultrasound image and an external image based on a predetermined reference coordinate system, through the input unit 500. Accordingly, the ultrasound probe P may be moved by a user, and an ultrasound image of an object and an external image registered with the ultrasound image may be displayed on the display unit 400 in correspondence to the movement of the ultrasound probe P.

That is, an image that is displayed on the display unit 400 may change according to movement of the ultrasound probe P. The image that changes in correspondence to the movement of the ultrasound probe P may be an ultrasound image of an object that is observed in real time, or an external image corresponding to the ultrasound image. At this time, only the ultrasound image may be changed and displayed in correspondence to the movement of the ultrasound probe P according to a user's input, or only the external image may be changed and displayed in correspondence to the movement of the ultrasound probe P according to a user's input.

Also, if a user's input confirming that an ultrasound image matches with an external image corresponding to the ultrasound image and is accurately registered with the external image is received, the ultrasound image and the external image may be synchronized and displayed on the display unit 400, so that the ultrasound image and the external image synchronized with each other can be simultaneously changed and displayed in correspondence to movement of the ultrasound probe P.

The main body M may include, as shown in FIG. 2, a beamformer 100, an image processor 200, a storage unit 300, the display unit 400, the input unit 500, a controller 600, and the tracking unit 700.

The beamformer 100 may beamform an ultrasonic signal so that the ultrasound probe P can irradiate ultrasonic waves, or may beamform an ultrasonic echo signal received from the ultrasound probe P. Herein, beamforming may mean a method of delaying and arranging ultrasonic waves irradiated to a specific location of an object or echo ultrasonic waves reflected from a specific location of an object. The beamforming is used to compensate for time differences with which ultrasonic waves arrived at a specific location of an object or echo ultrasonic waves reflected from a specific location of an object arrive at the plurality of transducer elements.

The beamformer 100 may include a transmit beamformer 110 configured to beamform ultrasonic waves that are irradiated to an object, and a receive bemformer 120 configured to beamform collected echo ultrasonic waves.

The beamformer 100 may adopt one of well-known beamforming methods, or may use two or more of the well-known beamforming methods in combination or selectively. Also, an ultrasonic echo signal beamformed by the beamformer 100 may be transferred to the image processor 200, which will be described later, and used to create an ultrasound image.

The image processor 200 may process the ultrasonic echo signal beamformed by the beamformer 100 to create an ultrasound image of the object, and transfer the ultrasound image to the display unit 400, which will be described later, to visually provide the user with anatomical information about the object. The image processor 200 may process the echo ultrasonic signal according to one of well-known image processing methods. For example, the image processor 200 may perform Time Gain Compensation (TGC) on the beamformed echo ultrasonic signal. Then, the image processor 200 may set a Dynamic Range (DR). After the image processor 200 sets the DR, the image processor 200 may compress the echo ultrasonic signal of the set DR. Finally, the image processor 200 may rectify the echo ultrasonic signal to remove noise from the echo ultrasonic signal. The image processor 200 may create an ultrasound image using the processed echo ultrasonic signal. The image processor 200 may create various kinds of ultrasound images. The ultrasound images that are created by the image processor 200 may include an Amplitude (A)-mode image, a Brightness (B)-mode image, a Motion (M)-mode image, and a Doppler (D)-mode image. For creating such various kinds of ultrasound images, the image processor 200 may be implemented in the form of hardware such as a microprocessor, or in the form of software that can be executed on hardware.

The storage unit 300 may store an external image of an object acquired by an external imaging device. Particularly, the storage unit 300 may store a volume image of an object including volume information of the object. Also, the storage unit 300 may store a 3D volume image of an object in which the object is represented in coronal, sagittal, and axial directions, and also may slice the 3D volume image into 2D images, that is, planar images to store the planar images.

For example, the storage unit 300 may store a CT image of an object acquired by a CT scanner or a MR image of an object acquired by a MRI scanner.

Also, the storage unit 300 may store various kinds of information for controlling the ultrasound imaging apparatus 1. For example, the storage unit 300 may store a registration parameter that is used to register ultrasound images with external images.

The storage unit 300 may be implemented as at least one kind of storage medium, among a flash memory type, a hard disk type, a multimedia card micro type, card type memory (for example, Secure Digital (SD) memory or eXtreme Digital (XD) memory), Random Access Memory (RAM), Static Random Access Memory (SRAM), Read-Only Memory (ROM), Electrically Erasable Programmable Read-Only Memory (EEPROM), and Programmable Read-Only Memory (PROM), magnetic memory, a magnetic disk, and an optical disk.

In FIG. 2, a case in which the storage unit 300 is included in the main body M is shown. However, according to another embodiment, the storage unit 300 may be coupled with the main body M through an external interface. Unlike this, the storage unit 300 may be implemented as an external server that forms a common network with the ultrasound imaging apparatus 1.

The display unit 400 may display an ultrasound image created by the image processor 200. A user may visually recognize anatomical information about the object through the ultrasound image displayed on the display unit 400.

Also, the display unit 400 may display an external image stored in the storage unit 300. Particularly, if the external image includes a volume image of an object, the display unit 400 may display one of slice images of the object configuring the volume image of the object.

Also, the display unit 400 may display an ultrasound image and an external image at the same time. At this time, the display unit 400 may display an ultrasound image and an external image registered with the ultrasound image, at the same time.

In FIG. 1, a case in which the display unit 400 is a single display is shown. However, according to another embodiment, the display unit 400 may include a plurality of displays. In this case, an ultrasound image may be displayed on one of the plurality of displays, and an external image may be displayed on another one of the plurality of displays.

Also, the display unit 400 may display a first reference line overlapping an ultrasound image of an object acquired through the ultrasound probe P, and also display a second reference line overlapping an external image corresponding to the ultrasound image of the object. Also, the display unit 400 may display the first reference line and the second reference line in the form of grids formed with at least ones of straight lines and curved lines. Also, the display unit 400 may display at least one of a character, a symbol, a numeral, and a figure around the first reference line and the second reference line displayed on the display panel, or at an intersection of the first reference line and the second reference line. Also, the display unit 400 may display the first reference line and the second reference line with the same color or with different colors according to the brightness of the entire or a part of the ultrasound image or the brightness of the entire or a part of the external image, upon registering the ultrasound image with the external image.

Also, the display unit 400 may display a reference point for accurately registering an ultrasound image input through the input unit 500 with an external image. The reference point means a point that is used as a standard for a user to register one of an ultrasound image and an external image with the other one. For example, there is a case in which a user observes an object (for example, a liver) using the ultrasound probe P to find a tumor at the right part of the liver from an ultrasound image so that the user wants to register the ultrasound image with an external image based on the tumor. In this case, if an input for setting the tumor at the right part of the liver to a reference point is received through the input unit 500, the reference point may be displayed on the display unit 400. Herein, reference points set according to a user's input with respect to an ultrasound image may be defined as first reference points, and reference points set according to a user's input with respect to an external image may be defined as second reference points.

The display unit 400 may display a first reference point with respect to an ultrasound image or a second reference point with respect to an external image, as at least one point, according to a user's input. If a plurality of user inputs for setting a plurality of reference points are received, the display unit 400 may display a plurality of points. Also, a mark representing a reference point on the display unit 400 may be at least one of a character, a symbol, a numeral, and a figure.

The input unit 500 may be provided on the main body M to receive commands related to operations of the ultrasound imaging apparatus 1. For example, the input unit 500 may receive a diagnosis start command and a mode selection command.

Also, the input unit 500 may receive a reference point selection command for accurate registration between an ultrasound image and an external image. Also, the input unit 500 may receive a user selection command for matching an ultrasound image with an external image, upon registering the ultrasound image with the external image. For example, if a user selects at least one of an ultrasound image and an external image through the input unit 500 to set a reference point, the selected image including the selected reference point may be displayed as a fixed image on the display unit 400, without changing in correspondence to movement of the ultrasound probe P.

The input unit 500 may be one of various kinds of input means, such as a keyboard, a mouse, a trackball, a tablet PC, and a touch screen module, through which a user can input control commands.

The controller 600 may control individual components of the ultrasound imaging apparatus 1 according to a user's control command input through the input unit 500 or according to internal computation.

In order to register an ultrasound image with an external image, the controller 600 may acquire information about the position and direction of an object using the ultrasound probe P, and control the image processor 200 to create an ultrasound image based on the information about the position and direction of the object.

Also, the controller 600 may register an ultrasound image generated by the image processor 200 with an external image stored in the storage unit 300, and then control the display unit 400 to display the registered images.

Specifically, the controller 600 may acquire a transform matrix for registration. More specifically, the controller 600 may acquire a rotation transform matrix for rotating the axis of coordinates, and a position transform matrix for moving the position of the axis of coordinates.

Hereinafter, a method of acquiring a rotation transform matrix will be first described, and then a method of acquiring a position transform matrix will be described.

In order to acquire the rotation transform matrix, the controller 600 may set a reference coordinate system, and transform a coordinate system that is applied to an ultrasound image to the reference coordinate system. Herein, the reference coordinate system may be a coordinate system of which the origin is the position of the tracking unit 700 of generating electro-magnetic waves to track the controlled part P1 of the ultrasound probe P.

Then, the input unit 500 may receive a control command for selecting a slice image of an object at a specific position in an external image, from a user. Preferably, a user may view an ultrasound image of an object displayed on the display unit 400 when the ultrasound probe P is positioned over the object, and select an external slice image of the object corresponding to the position of the displayed ultrasound image from an external volume image of the object.

Then, the controller 600 may transform a coordinate system that is applied to the selected slice image of the object to a coordinate system on the entire volume image. The coordinate system on the volume image may be formed in the coronal, sagittal, and axial directions.

Finally, the controller 600 may acquire a rotation transform matrix for transforming the reference coordinate system to the coordinate system on the volume image. In order to acquire the rotation transform matrix, the controller 600 may calculate a degree of tilting (that is, a rotation angle) of the coordinate system on the volume image with respect to the reference coordinate system.

After the controller 600 acquires the rotation transform matrix, the input unit 500 may receive a reference point selection command for selecting a reference point representing the same anatomical position on the ultrasound image and the slice image, from the user. For example, the user may select a reference point from the ultrasound image, and then select a reference point located at the same anatomical position as the reference point, from the external image. On the contrary, the user may select a reference point from the external image, and then select a reference point located at the same anatomical position as the reference point, from the ultrasound image.

In the following description, for convenience of description, a case of selecting a reference point of an ultrasound image and then selecting a reference point of an external image will be described.

If the reference points are selected, the controller 600 may transform coordinates of the reference point with respect to the ultrasound image into coordinates on a reference coordinate system. Since information about the position and direction of the ultrasound probe P can be acquired through the tracking unit 700, the controller 600 can acquire coordinates of the reference point of the ultrasound image on the reference coordinate system using the information about the position and direction of the ultrasound probe P.

Also, the controller 600 may transform coordinates of the reference point on the external image into coordinates on the coordinate system of the volume image.

Finally, the controller 600 may acquire a translational transform matrix for transforming the reference coordinate system to the coordinate system on the volume image. In order to acquire the translational transform matrix, the controller 600 may calculate differences between the coordinates of the reference point of the ultrasound image on the reference coordinate system and the coordinates of the reference point of the external image on the coordinate system of the volume image.

After the controller 600 acquires the translational transform matrix according to the above-described process, the controller 600 may register the external image with the displayed ultrasound image in real time. Also, the controller 600 may control the display unit 400 to display the registered ultrasound image and external image together.

Also, if a command for selecting a first reference point of the ultrasound image is received from the user in order to more accurately match (that is, re-register) the ultrasound image with the external image registered with the ultrasound image, the controller 600 may fix the ultrasound image including the first reference point, and change the external image that is to be more accurately registered with the ultrasound image, according to movement of the ultrasound probe P. Also, if a registration completion command is received from the user through the input unit 500, the controller 600 may determine whether the fixed ultrasound image including the first reference point matches with the external image that is displayed in correspondence to the movement of the ultrasound probe P adjusted by the user, based on the first reference line and the second reference line respectively displayed on the ultrasound image and the external image. If the controller 600 determines that the fixed ultrasound image matches with the external image, the controller 600 may control the display unit 400 to synchronize the ultrasound image with the external image and then to display the ultrasound image and the external image.

Meanwhile, if a command for selecting a second reference point of the external image is received from the user, the controller 600 may fix the external image including the second reference point, and change the ultrasound image that is to be more accurately registered with the external image, according to movement of the ultrasound probe P. Also, if a registration completion command is received from the user through the input unit 500, the controller 600 may determine whether the fixed external image including the second reference point matches with the ultrasound image that is displayed in correspondence to the movement of the ultrasound probe P adjusted by the user, based on the first reference line and the second reference line respectively displayed on the ultrasound image and the external image. If the controller 600 determines that the fixed external image matches with the ultrasound image, the controller 600 may control the display unit 400 to synchronize the ultrasound image with the external image and then to display the ultrasound image and the external image.

The tracking unit 700 may sense electro-magnetic waves generated by the controlled part P1 to track the position of the ultrasound probe P. Also, the tracking unit 700 may receive information about the position and direction of the ultrasound probe P, acquired through various kinds of sensors of the controlled part P1, in the form of an electrical signal, and track the position of the ultrasound probe P based on the electrical signal.

Figure 3:
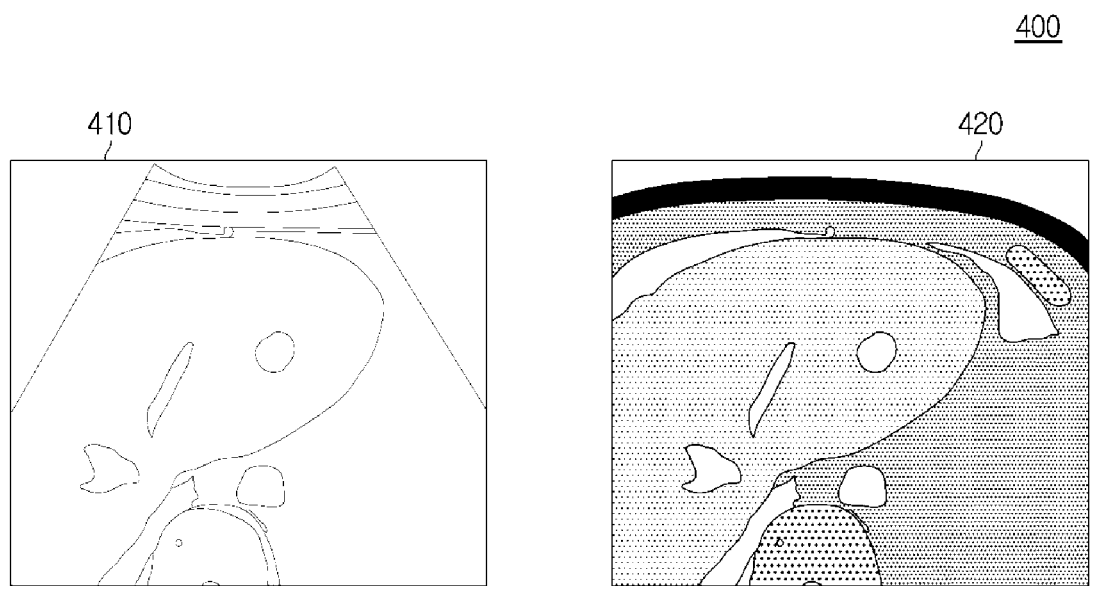
FIG. 3 shows an ultrasound image and an external image registered with the ultrasound image, displayed on a display unit according to an embodiment of the present disclosure.

FIG. 3 shows an ultrasound image and an external image registered with the ultrasound image, displayed on the display unit 400 according to an embodiment of the present disclosure. In FIG. 3, a case in which the ultrasound image is registered with the external image without any errors is shown.

The display unit 400 may display the ultrasound image in a predetermined first area 410, and the external image registered with the ultrasound image in a predetermined second area 420. The ultrasound image of the first area 410 and the external image of the second area 420 may be displayed on a display panel or on a plurality of display panels.

More specifically, referring to FIG. 3, the display unit 400 may display an ultrasound image acquired through the ultrasound probe P in the first area 410, and an external image corresponding to the ultrasound image in the second area 420. The external image may be a planar image sliced from a 3D volume image stored in the storage unit 300, the planar image corresponding to the ultrasound image.

Figure 4:
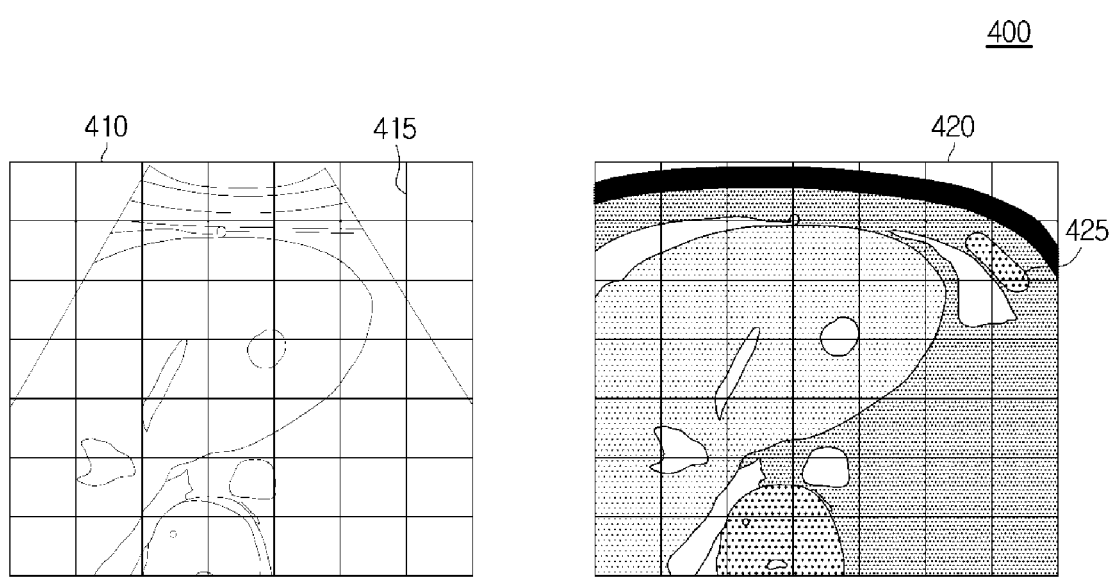
FIG. 4 shows an ultrasound image and an external image registered with the ultrasound image, displayed on a display unit according to an embodiment of the present disclosure, wherein reference lines overlap the ultrasound image and the external image.
Figure 5A:
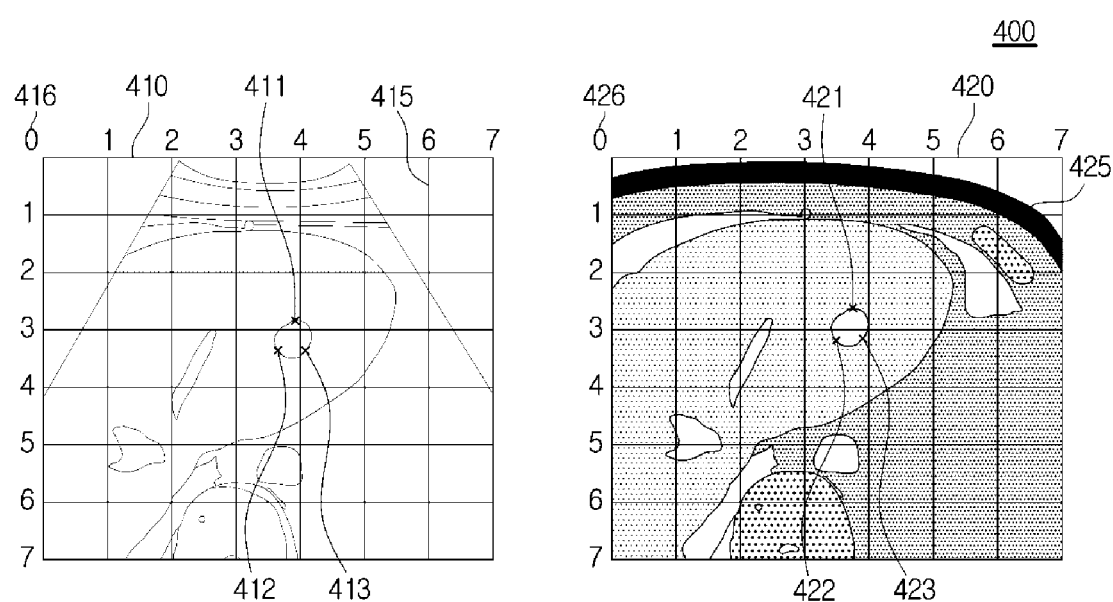
FIG. 5A shows an ultrasound image and an external image registered with the ultrasound image, displayed on a display unit according to an embodiment of the present disclosure, wherein reference lines with numerals overlap the ultrasound image and the external image.
Figure 5B:
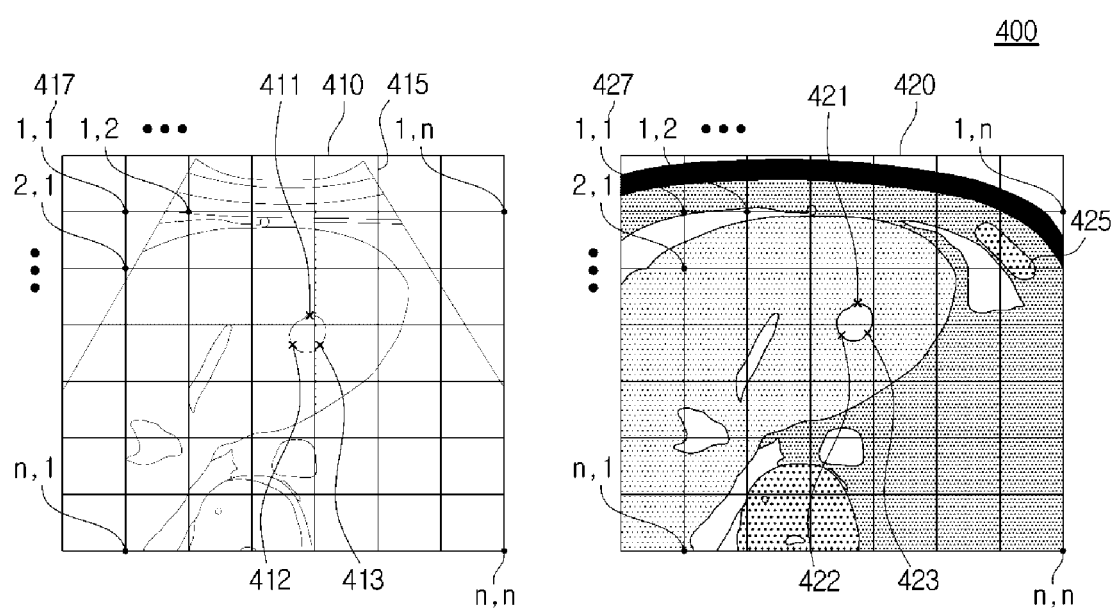
FIG. 5B shows an ultrasound image and an external image registered with the ultrasound image, displayed on a display unit according to an embodiment of the present disclosure, wherein reference lines overlap the ultrasound image and the external image, and numerals are displayed in the form of coordinates at intersections of the reference lines.
Figure 5C:
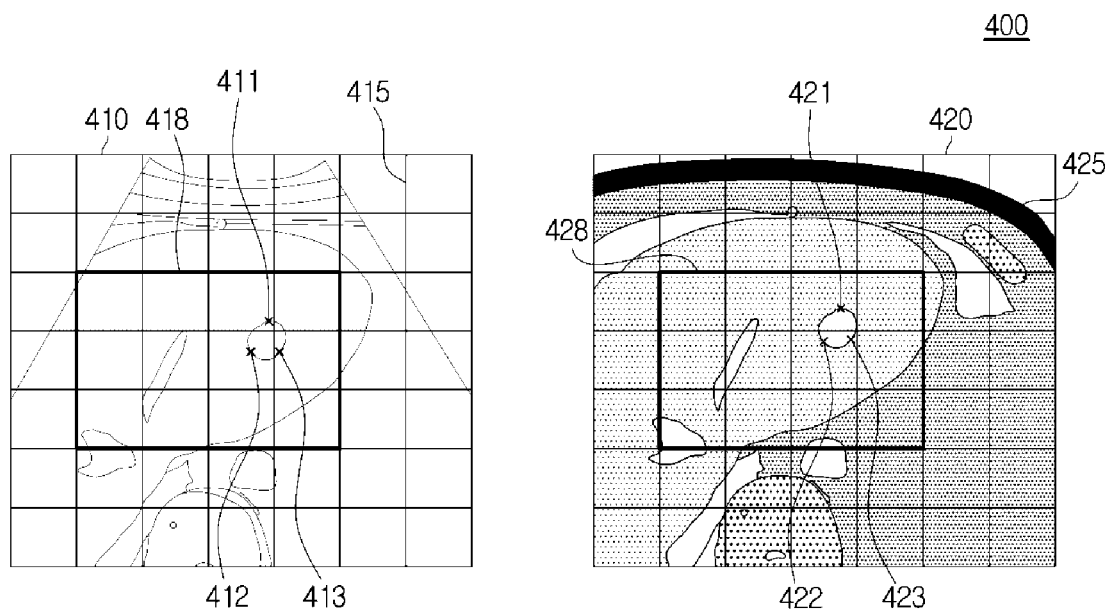
FIG. 5C shows an ultrasound image and an external image registered with the ultrasound image, displayed on a display unit according to an embodiment of the present disclosure, wherein reference lines overlap the ultrasound image and the external image with the same color or different colors.

FIG. 4 shows an ultrasound image and an external image registered with the ultrasound image, displayed on the display unit 400 according to an embodiment of the present disclosure, wherein reference lines overlap the ultrasound image and the external image. FIGS. 5A, 5B, and 5C show an ultrasound image and an external image registered with the ultrasound image, displayed on the display unit 400 according to an embodiment of the present disclosure, wherein reference lines and numerals are displayed on the display unit 400 in order to more accurately match the ultrasound image with the external image. The following description related to FIGS. 4 to 5C will be given under the assumption that there is an error between the anatomical position of the ultrasound image and the anatomical position of the external image.

The display unit 400 may display, as shown in FIG. 4, a plurality of first reference lines 415 overlapping an ultrasound image 410 of an object acquired through the ultrasound probe P, and also may display a plurality of second reference lines 425 overlapping an external image 420 corresponding to the ultrasound image 410 of the object. The first reference lines 415 and the second reference lines 425 may be displayed in the form of grids formed with at least ones of straight lines and curved lines. Also, a user may apply a predetermined input through the input unit 500 to control the display unit 400 to display or not to display the first reference lines 415 and the second reference lines 425.

Also, the display unit 400 may further display at least one(s) of characters, symbols, numerals, and figures, around the first reference lines 415 and the second reference lines 425, or at the intersections of the first reference lines 415 and the second reference lines 425.

For example, the display unit 400 may further display, as shown in FIG. 5A, a plurality of numerals 416 around the first reference lines 415 overlapping the ultrasound image 410. Also, the display unit 400 may further display a plurality of numerals 426 around the second reference lines 425 overlapping the external image 420. Also, the display unit 400 may display, as shown in FIG. 5B, a plurality of numerals in the form of coordinates at intersections (1, 1), (1, 2), . . . , (n, n) 417 of the first reference lines 415 overlapping the ultrasound image 410. Also, the display unit 400 may display a plurality of numerals in the form of coordinates at intersections (1, 1), (1, 2), . . . , (n, n) 427 of the second reference lines 425 overlapping the external image 420.

Also, the display unit 400 may display the first reference lines 415 overlapping the ultrasound image 410 and the second reference lines 425 overlapping the external image 420 with the same color or with different colors according to a change in brightness of the entire or a part of the ultrasound image 410 and the external image 420.

For example, if an area 418 to be compared is selected from the ultrasound image 410 by the user, as shown in FIG. 5C, the display unit 400 may change the color of the corresponding reference lines 415 to a color stored in correspondence to the brightness of the area 418. Also, if an area 428 to be compared is selected from the external image 420 by the user, the display unit 400 may change the color of the corresponding reference lines 425 to a color stored in correspondence to the brightness of the area 428.

As described above, FIGS. 4 to 5C relate to user interfaces that are displayed on the display unit 400, as means for more accurately and quickly re-registering the ultrasound image 410 with the external image 420 registered with the ultrasound image 410 using the ultrasound probe P.

The user may accurately and quickly perform re-registration based on a user interface that is displayed on the display unit 400. Hereinafter, a case of registering the external image 420 with the fixed ultrasound image 410 will be described with reference to FIGS. 5A to 5C. Referring to FIG. 5A, the user can accurately recognize positions of reference points 411, 412, and 413 of the ultrasound image 410, which are used as standards for registration, based on the numerals 416 displayed around the first reference lines 415 (for example, the positions of the reference points 411, 412, and 413 can be recognized as coordinate values (4, 4) of the first reference lines 415 corresponding to a numeral 4 on the horizontal axis and a numeral 4 on the vertical axis). Then, the user may rotate or move the external image 420 using the ultrasound probe P to match points 421, 422, and 423 of the external image 420 corresponding to the reference points 411, 412, and 413 of the ultrasound image 410, with numerals 426 (that is, coordinate values (4, 4) of the second reference lines 425 representing a numeral 4 on the horizontal axis and a numeral 4 on the vertical axis, corresponding to the first reference lines 415) displayed around the second reference lines 425 displayed on the external image 420, thereby conveniently and quickly registering the external image 420 with the ultrasound image 410.

Also, referring to FIG. 5B, the user can accurately recognize the positions of the reference points 411, 412, and 413 of the ultrasound image 410, which are used as standards for registration, based on numeral coordinates 417 displayed at the intersections of the first reference lines 415 (for example, the positions of the reference points 411, 412, and 413 can be recognized as coordinate values (4, 4) of the first reference lines 415 corresponding to a numeral 4 on the horizontal axis and a numeral 4 on the vertical axis). Then, the user may rotate or move the external image 420 using the ultrasound probe P to match points 421, 422, and 423 of the external image 420 corresponding to the reference points 411, 412, and 413 of the ultrasound image 410, with numeral coordinates 427 (that is, coordinate values (4, 4) of the second reference lines 425 representing a numeral 4 on the horizontal axis and a numeral 4 on the vertical axis, corresponding to the first reference lines 415) displayed at the intersection of the second reference lines 425 displayed on the external image 420, thereby conveniently and quickly registering the external image 420 with the ultrasound image 410.

Also, referring to FIG. 5C, the user may recognize a color of the first reference lines 415 corresponding to the brightness of an area 418 including the reference points 411, 412, and 413 of the ultrasound image 410, when the color of the first reference lines 415 is displayed on the display unit 400, and then match the brightness of the external image 420 with the brightness of the ultrasound image 410 through the input unit 500. Thereafter, when the external image 420 changes in correspondence to movement of the ultrasound probe P, the brightness of the external image 420 may change accordingly, so that the color of the second reference lines 425 can change in correspondence to the change in brightness of the external image 420. Accordingly, the user may match the color of the first reference lines 415 corresponding to the brightness of the area 418 including the reference points 411, 412, and 413 of the ultrasound image 410, with the color of the second reference lines 425 changing according to the brightness of the external image 420 in correspondence to movement of the ultrasound probe P, thereby conveniently and quickly re-registering the ultrasound image 410 with the external image 420.

The above description relates to an example of a method of matching (re-registering) an external image with a fixed ultrasound image using various user interfaces displayed on the display unit 400. However, a method of matching (re-registering) an ultrasound image with a fixed external image is also possible.

Figure 7:
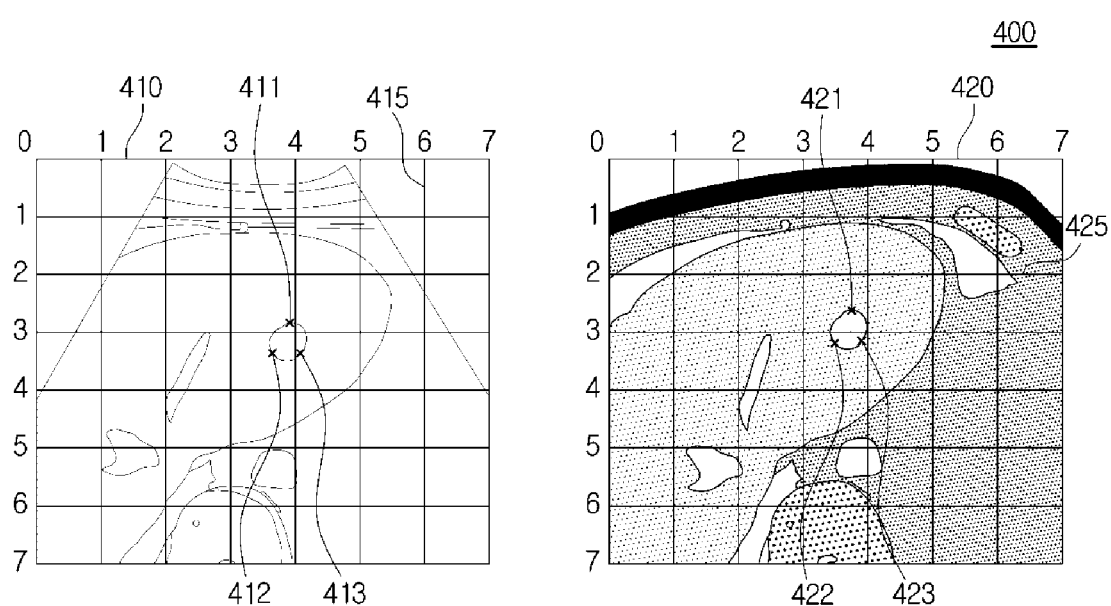
FIG. 7 is a view for describing a method of registering an external image with an ultrasound image based on reference points of the ultrasound image displayed on a display unit according to an embodiment of the present disclosure.

FIG. 6 is a flowchart illustrating a method of accurately and quickly re-registering an ultrasound image with an external image registered with the ultrasound image, on the display unit 400. Also, FIG. 7 is a view for describing a method of matching (re-registering) an external image with an ultrasound image based on reference points of the ultrasound image displayed on the display unit 400 according to an embodiment of the present disclosure. Also, FIG. 8 shows reference lines displayed on the display unit 400 according to an embodiment of the present disclosure, and other reference lines changing in correspondence to movement of the ultrasound probe P.

Hereinafter, a method in which a user accurately and quickly matches (re-registers) an ultrasound image 410 with an external image 420 registered with the ultrasound image 410 using the ultrasound probe P, when the display unit 400 displays the ultrasound image 410 and the external image 420 will be described with reference to FIGS. 6 to 12.

The user may move the ultrasound probe P to perform ultrasonic diagnosis. Then, the display unit 400 may display an ultrasound image for the position of an object corresponding to the movement of the ultrasound probe P, and simultaneously display an external image registered with the ultrasound image in real time.

At this time, a registration error may be generated between the ultrasound image 410 and the external image 420. The registration method as described above may be based on image registration with respect to a rigid body, however, since a real human body is a nonrigid object, the accuracy of registration may be lowered.

For example, there are cases in which the coordinate system changes due to movement of an object such as breathing, in which registration with respect to an object image including a plurality of reference points is performed, and in which an error occurs in selecting reference points on a volume image. In these cases, inaccurate registration may be performed.

Particularly, when an object to be scanned is a large organ such as a liver, it may be difficult to acquire an ultrasound image of the entire object by scanning the object one time. Accordingly, an error in anatomical position may be generated in selecting a reference point, resulting in a registration error.

In this case, initial registration may be performed on an organ such as a blood vessel from which a reference point can be relatively accurately selected, and then a reference point may be again selected from the adjacent object to perform re-registration. Upon the re-registration, a rotation transform matrix according to a rotation angle as described above may be maintained, and a translational transform matrix that is acquired based on a difference between the coordinates of reference points of two images may be again calculated.

The ultrasound imaging apparatus 1 may display an ultrasound image and an external image registered by a predetermined transform matrix. More specifically, the controller 600 of the ultrasound imaging apparatus 1 may acquire a transform matrix for registration, and register an ultrasound image with an external image using the transform matrix. Then, the display unit 400 of the ultrasound imaging apparatus 1 may display the ultrasound image and the external image registered with the ultrasound image at the same time in real time, in operation 1000.

As such, two images may be not accurately registered even after image registration is performed. In this case, re-registration for accurately matching the two images may be performed. However, in this case, a registration error may be generally not great. Accordingly, the ultrasound image and the external image may be quickly and conveniently registered using the ultrasound probe P, without any input through the input unit 500.

If the user determines that registration of the ultrasound image 410 with the external image is inaccurate, the user may input a re-registration command through the input unit 500 in order to request the display unit 400 to register the ultrasound image 410 for the object with the external image 420 corresponding to the ultrasound image 410 and display the ultrasound image 410 and the external image 420.

If the re-registration command is input by the user, the display unit 400 may display the first reference lines 415 overlapping the ultrasound image 410, and the second reference lines 415 overlapping the external image 420, as shown in FIG. 7, in operation 1100. Then, the user may select one or more reference points 411, 412, and 413 from at least one of the ultrasound image 410 and the external image 420 in order to decide a reference image for re-registration, in operation 1200.

First, if the user wants to register the external image 420 based on the ultrasound image 410, the user may input a command for selecting three points of the ultrasound image 410 as the first reference points 411, 412, and 413 of the ultrasound image 410, through the input unit 500. If the command is input, the controller 600 may fix the ultrasound image 410 including the first reference points 411, 412, and 413, regardless of movement of the ultrasound probe P, and change the external image 420 that is to be accurately registered with the ultrasound image 410, in correspondence to movement of the ultrasound probe P, in operation 1300.

Thereafter, the user may move the ultrasound probe P, and the tracking unit 700 may sense the controlled part P1 of the ultrasound probe P to transmit information about the position and direction of the ultrasound probe P, in the form of an electrical signal, to the controller 600. The controller 600 may receive the information about the position and direction of the ultrasound probe P, and rotate or move the external image 420 based on the information about the position and direction of the ultrasound probe P so that the external image 420 can be displayed on the display unit 400 in correspondence to the movement of the ultrasound probe P.

The user may move and adjust the ultrasound probe P until the ultrasound image 410 matches with the external image 420 based on the first reference lines of the ultrasound image 410 and the second reference lines of the external image 420, to move or rotate the external image 420, thereby matching the external image 420 with the fixed ultrasound image 410. That is, the user may re-register the external image 420 with the fixed ultrasound image 410. The user may use various interface screens displayed on the display unit 400 in order to accurately match the ultrasound image 410 with the external image 420 registered with the ultrasound image 410, as described above with reference to FIGS. 5A, 5B, and 5C.

The user may input a re-registration completion command through the input unit 500 after the re-registration process using the ultrasound probe P. If the controller 600 receives a re-registration completion command from the user through the input unit 500, the controller 600 may determine whether the external image 420 changed in correspondence to the movement of the ultrasound probe P adjusted by the user matches with the fixed ultrasound image 410, based on the first reference lines 415 and the second reference lines 425 respectively displayed on the ultrasound image 410 and the external image 420.

Also, if the controller 600 determines that the external image 420 matches with the ultrasound image 410, the controller 600 may determine that re-registration is completed. Then, the controller 600 may synchronize the ultrasound image 410 with the external image 420 so that the ultrasound image 410 and the external image 420 can change together in correspondence to movement of the ultrasound probe P, in operation 1400.

Also, if the user wants to register the ultrasound image 410 based on the external image 420, the user may input a command for selecting three points of the external image 420 as the second reference points 421, 422, and 423 of the external image 420, through the input unit 500. If the command is input, the controller 600 may fix the external image 420 including the second reference points 421, 422, and 423, regardless of movement of the ultrasound probe P, and change the ultrasound image 410 that is to be accurately registered with the external image 420, in correspondence to movement of the ultrasound probe P, in operation 1300.

Thereafter, the user may move the ultrasound probe P, and the tracking unit 700 may sense the controlled part P1 of the ultrasound probe P to transmit information about the position and direction of the ultrasound probe P, in the form of an electrical signal, to the controller 600. The controller 600 may receive the information about the position and direction of the ultrasound probe P, and rotate or move the ultrasound image 410 based on the information about the position and direction of the ultrasound probe P so that the ultrasound image 410 can be displayed on the display unit 400 in correspondence to movement of the ultrasound probe P.

The user may move and adjust the ultrasound probe P until the ultrasound image 410 matches with the external image 420 based on the first reference lines of the ultrasound image 410 and the second reference lines of the external image 420, to move or rotate the ultrasound image 410, thereby matching the ultrasound image 410 with the fixed external image 420. That is, the user may re-register the ultrasound image 410 with the fixed external image 420. At this time, the user may use various interface screens displayed on the display unit 400 in order to accurately match the ultrasound image 410 with the external image 420 registered with the ultrasound image 410, as described above with reference to FIGS. 5A, 5B, and 5C.

The user may input a re-registration completion command through the input unit 500 after the re-registration process using the ultrasound probe P. If the controller 600 receives a re-registration completion command from the user through the input unit 500, the controller 600 may determine whether the external image 420 (or the ultrasound image 410) changed in correspondence to the movement of the ultrasound probe P adjusted by the user matches with the fixed ultrasound image 410 (or the fixed external image 420), based on the first reference lines 415 and the second reference lines 425 respectively displayed on the ultrasound image 410 and the external image 420.

Also, if the controller 600 determines that the external image 420 (or the ultrasound image 410) matches with the ultrasound image 410 (or the external image 420), the controller 600 may determine that re-registration is completed. Then, the controller 600 may synchronize the ultrasound image 410 with the external image 420 so that the ultrasound image 410 and the external image 420 can change together in correspondence to movement of the ultrasound probe P, in operation 1400.

In detail, a process of more accurately matching (re-registering) the ultrasound image 410 with the external image 420 registered with the ultrasound image 410 will be described with reference to FIG. 7, as follows. First, a case of fixing the ultrasound image 410 and re-registering the external image 420 based on the ultrasound image 410 will be described. In FIG. 7, a case in which reference points 411, 412, and 413 selected by the user from the fixed ultrasound image 410 exist around an intersection (4, 3) of the first reference lines 415, and points 421, 422, and 423 of the registered external image 420 corresponding to the reference points 411, 412, and 413 exist to the left of an intersection (4, 3) of the second reference lines 425 is shown. This case corresponds to when the ultrasound image 410 is not accurately registered with the external image 410. Accordingly, the user may use the ultrasound probe P to move any one of the ultrasound image 410 and the external image 420. More specifically, the tracking unit 700 may sense the controlled part P1 of the ultrasound probe P, and transmit information about the position and direction of the ultrasound probe P, in the form of an electrical signal, to the controller 600. The controller 600 may receive the information about the position and direction of the ultrasound probe P, and rotate or move the external image 420 based on the information about the position and direction of the ultrasound probe P so as to display the external image 420 on the display unit 400 in correspondence to the movement of the ultrasound probe P, thereby matching the points 421, 422, and 423 of the external image 420 with the points 411, 412, and 413 around the intersection (4, 3) of the first reference lines 415 of the ultrasound image 410.

Then, the case of fixing the external image 420 and re-registering the ultrasound image 410 based on the external image 420 will be described. As shown in FIG. 7, the reference points 421, 422, and 423 selected by the user from the fixed external image 420 may exist to the left of the intersection (4, 3) of the second reference lines 425, and points 411, 412, and 413 of the registered ultrasound image 410 corresponding to the reference points 421, 422, and 423 may exist around an intersection (4, 3) of the first reference lines 415. This case corresponds to when the ultrasound image 410 is not accurately registered with the external image 410. Accordingly, the user may use the ultrasound probe P to move any one of the ultrasound image 410 and the external image 420. More specifically, the tracking unit 700 may sense the controlled part P1 of the ultrasound probe P, and transmit information about the position and direction of the ultrasound probe P, in the form of an electrical signal, to the controller 600. The controller 600 may receive the information about the position and direction of the ultrasound probe P, and rotate or move the ultrasound image 410 based on the information about the position and direction of the ultrasound probe P so as to display the ultrasound image 410 on the display unit 400 in correspondence to the movement of the ultrasound probe P, thereby matching the points 411, 412, and 413 of the ultrasound image 410 with the points 421, 422, and 423 located to the left of the intersection (4, 3) of the second reference lines 425 of the external image 420.

Also, referring to FIG. 8, the display unit 400 may display a plurality of third reference lines 419, in addition to the first reference lines 415 displayed on the ultrasound image 410. The third reference lines 419 may be displayed in the form of dotted lines. The third reference lines 419 may be moved or adjusted according to a direction of rotation or a direction of movement of the ultrasound image 410 that is displayed in correspondence to movement of the ultrasound probe P, unlike the fixed first reference lines 415. Accordingly, the user may easily recognize a direction of rotation or a direction of movement of the ultrasound image 410 rotating or moving in correspondence to movement of the ultrasound probe P through such an auxiliary indicator as the third reference lines 419. Also, the display unit 400 may display a plurality of fourth reference lines 429, in addition to the second reference lines 425 displayed on the external image 42. The fourth reference lines 429 may be also displayed in the form of dotted lines. Also, the fourth reference lines 429 may be moved or adjusted according to a direction of rotation or a direction of movement of the external image 420 that is displayed in correspondence to movement of the ultrasound probe P, unlike the fixed second reference lines 425. Accordingly, the user may easily recognize a direction of rotation or a direction of movement of the external image 420 rotating or moving in correspondence to movement of the ultrasound probe P through such an auxiliary indicator as the fourth reference lines 429.

Figure 9:
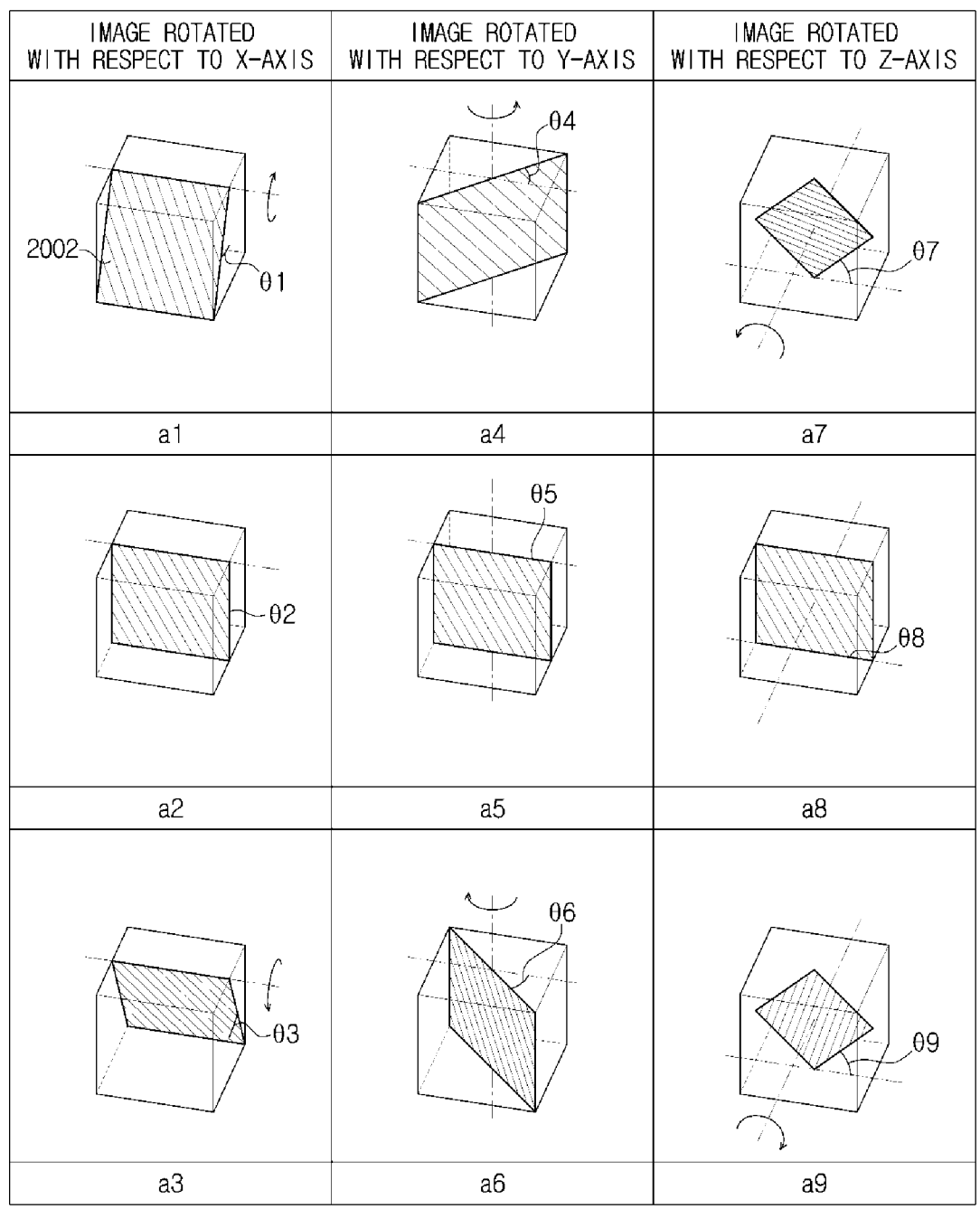
FIG. 9 relates to examples of showing rotation of an image according to movement of an ultrasound probe according to an embodiment of the present disclosure, using a cube.

FIG. 9 relates to examples of showing rotation of an image according to movement of the ultrasound probe P according to an embodiment of the present disclosure, using a cube.

The ultrasound image 410 and the external image 420 that are displayed on the display unit 400 of FIG. 8, as described above with reference to FIG. 8, are slice images. Accordingly, when two images mismatch with each other, a user may need to rotate any one of the images upon re-registration, in order to match the images. In this case, if information for guiding a direction of rotation and an angle of rotation of an image according to movement of the ultrasound probe P is provided through the display unit 400, the user will be able to easily match the ultrasound image 410 with the external image 420 upon re-registration.

A rotated image 2002 resulting from rotating an image using a cube, as shown in FIG. 9 (a1 to a9), may be displayed together with the ultrasound image 410 and the external image 420, at the lower or upper corner of the display unit 400. Also, the image 2002 in the cube may reflect movement or rotation of the ultrasound image 410 or the external image 420 in correspondence to manipulation of the ultrasound probe P.

Accordingly, when two images mismatch, the user may accurately recognize rotation information of an image according to manipulation of the ultrasound probe P from the image 2002 in the cube that is displayed on the display unit 400, thereby quickly and easily matching the images upon re-registration.

More specifically, examples of images rotated with respect to the x-axis may include an image a1 rotated by $\theta 1$ in a clockwise direction with respect to the x-axis, a reference image a2 not rotated, and an image a3 rotated by $\theta 3$ in a counterclockwise direction with respect to the x-axis. Also, examples of images rotated with respect to the y-axis may include an image a4 rotated by $\theta 4$ in the counterclockwise direction with respect to the y-axis, a reference image a5 not rotated, and an image a6 rotated by $\theta 6$ in the clockwise direction with respect to the y-axis. Also, examples of images rotated with respect to the z-axis may include an image a7 rotated by $\theta 7$ in the counterclockwise direction with respect to the z-axis, a reference image a8 not rotated, and an image a9 rotated by $\theta 9$ in the clockwise direction with respect to the z-axis.

For convenience of description, images rotated with respect to one of the x-axis, the y-axis, and the z-axis are shown, however, images may be rotated with respect to a plurality of axes.

Figure 10:
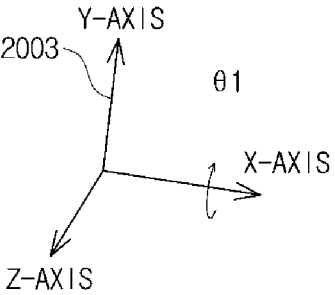
FIG. 10 relates to examples of showing rotation of an image according to movement of an ultrasound probe according to an embodiment of the present disclosure, on a reference coordinate system.

FIG. 10 relates to examples of showing rotation of an image according to movement of the ultrasound probe P according to an embodiment of the present disclosure, on a reference coordinate system.

Referring to FIG. 10, b1 to b9 may respectively correspond to a1 to a9 of FIG. 9. As shown in FIG. 10, information about a direction of rotation and an angle of rotation of an image rotating in correspondence to movement of the ultrasound probe P may be represented on a reference coordinate system.

Accordingly, like a1 to a9 of FIG. 9, a rotational coordinate system 2003 of an image based on the reference coordinate system (formed with the x-axis, the y-axis, and the z-axis) shown in FIG. 10 may be displayed together with the ultrasound image 410 and the external image 420, at the lower or upper corner of the display unit 400 described above. The rotational coordinate system 2003 may reflect movement or rotation of the ultrasound image 410 or the external image 420 in correspondence to manipulation of the ultrasound probe P.

Accordingly, when two images mismatch, the user may accurately recognize rotation information of an image according to movement of the ultrasound probe P from the reference coordinate system 2003 displayed on the display unit 400, thereby quickly and easily matching the images upon re-registration.

More specifically, examples of coordinate systems b1 to b3 rotated with respect to the x-axis may correspond to a1 to a3 of FIG. 9. The coordinate systems b1 to b3 may include a coordinate system b1 rotated by $\theta 1$ in a clockwise direction with respect to the x-axis, a coordinate system b2 not rotated, and a coordinate system b3 rotated by $\theta 3$ in a counterclockwise direction with respect to the x-axis. Also, examples of coordinate systems b4 to b6 rotated with respect to the y-axis may include a coordinate system b4 rotated by $\theta 4$ in the counterclockwise direction with respect to the y-axis, a coordinate system b5 not rotated, and a coordinate system b6 rotated by $\theta 6$ in the clockwise direction with respect to the y-axis. Also, examples of coordinate systems b7 to b9 rotated with respect to the z-axis may include a coordinate system b7 rotated by $\theta 7$ in the counterclockwise direction with respect to the z-axis, a coordinate system b8 not rotated, and a coordinate system b9 rotated by $\theta 9$ in the clockwise direction with respect to the z-axis. For convenience of description, coordinate systems rotated with respect to one of the x-axis, the y-axis, and the z-axis are shown, however, coordinate systems may be rotated with respect to a plurality of axes.

FIG. 11 relates to examples of showing rotation of an image according to movement of the ultrasound probe P according to an embodiment of the present disclosure, using dotted reference lines.

Referring to FIG. 11, c1 to c9 may correspond to a1 to a9 of FIG. 9 and b1 to b9 of FIG. 10. As shown in FIG. 11, information about a direction of rotation and an angle of rotation of an image rotating in correspondence to movement of the ultrasound probe P may be represented using a plurality of dotted reference lines 2005.

Accordingly, like a1 to a9 of FIG. 9, rotation information of an image represented using an image 2004 including the dotted reference lines 2005 shown in FIG. 11 (c1 to c9) may be displayed together with the ultrasound image 410 and the external image 420, at the lower or upper corner of the display unit 400 described above.

Also, the rotation information of the image may be displayed not as the separate image 2004, but as dotted reference lines (for example, the third and fourth reference lines 419 and 429 of FIG. 8) on the ultrasound image 410 and the external image 420. The reference lines 2005 of the separate image 2004 or the dotted reference lines (for example, the third and fourth reference lines 419 and 429 of FIG. 8) of the ultrasound image 410 and the external image 420 may reflect movement or rotation of the ultrasound image 410 or the external image 420 in correspondence to manipulation of the ultrasound probe P.

Accordingly, when two images mismatch, the user may accurately recognize rotation information of an image according to movement of the ultrasound probe P from the reference lines 2005 of the separate image 2004 output on the display unit 400 or the dotted reference lines (for example, the third and fourth reference lines 419 and 429 of FIG. 8) of the ultrasound image 410 and the external image 420, thereby quickly and easily matching the images upon re-registration.

More specifically, examples of images c1 to c3 rotated with respect to the x-axis may correspond to a1 to a3 of FIG. 9 and b1 to b3 of FIG. 10, and may include images c1 and c3 rotated with respect to the x-axis and an image c2 not rotated. Also, examples of images c4 to c6 rotated with respect to the y-axis may correspond to a4 to a6 of FIG. 9 and b4 to b6 of FIG. 10, and may include images c4 and c6 rotated with respect to the y-axis and an image c5 not rotated. Also, examples of images c7 to c9 rotated with respect to the z-axis may correspond to a7 to a9 of FIG. 9 and b7 to b9 of FIG. 10, and may include images c7 and c9 rotated with respect to the z-axis, and an image c8 not rotated. For convenience of description, images rotated with respect to one of the x-axis, the y-axis, and the z-axis are shown, however, images may be rotated with respect to a plurality of axes.

Figure 12:
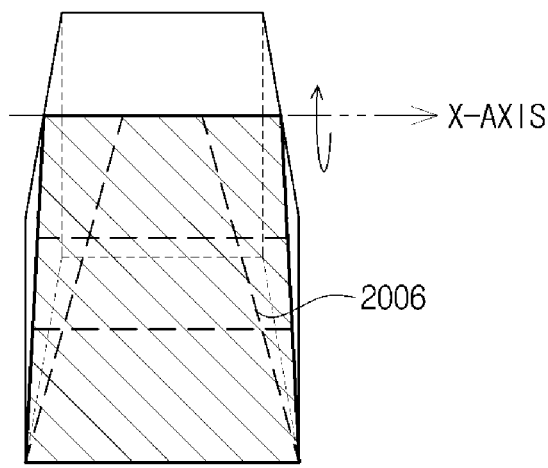
FIG. 12 relates to an example of showing rotation of an image according to movement of an ultrasound probe according to an embodiment of the present disclosure, using a cube and dotted reference lines.

FIG. 12 relates to an example of showing rotation of an image according to movement of the ultrasound probe P according to an embodiment of the present disclosure, using a cube and dotted reference lines.

Rotation information of an image represented using an image in a cube as shown in FIG. 9 and an image 2006 including dotted reference lines as shown in FIG. 11 may be displayed together with the ultrasound image 410 and the external image 420, at the lower or upper corner of the display unit 400 described above.

Also, the rotation information of the image represented using the image in the cube as shown in FIG. 9 and the image 2006 including the dotted reference lines as shown in FIG. 11 may reflect movement or rotation of the ultrasound image 410 or the external image 420 in correspondence to manipulation of the ultrasound probe P.

Accordingly, when two images mismatch, the user may accurately recognize rotation information of an image according to movement of the ultrasound probe P from the dotted reference lines and the image in the cube displayed on the display unit 400, thereby quickly and easily matching the images upon re-registration. In FIG. 12, for convenience of description, a case of rotating an image with respect to the x-axis is shown.

Figure 13:
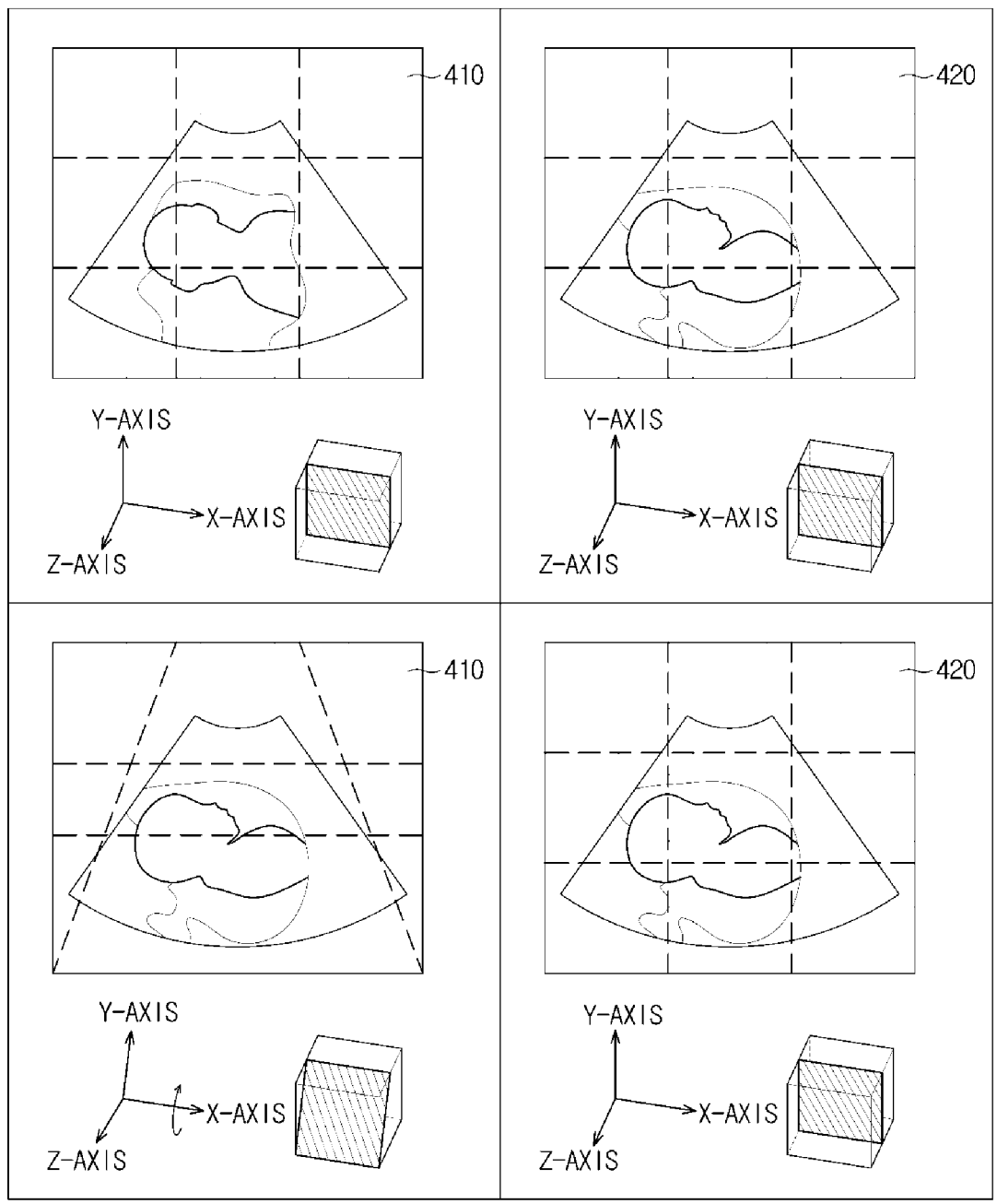
FIG. 13 shows an embodiment in which information about rotated images described above with reference to FIGS. 9 to 11 is displayed on a display unit.

FIG. 13 shows an embodiment in which information about rotated images described above with reference to FIGS. 9 to 11 is displayed on the display unit 400.

FIG. 13 shows examples in which when the ultrasound image 410 and the external image 420 are registered or re-registered as described above with reference to FIGS. 9 to 11, the images of FIGS. 9 to 11 representing rotation information of images may be displayed together with the ultrasound image 410 and the external image 420 on the display unit 400.

In the embodiment of FIG. 13, it is assumed that the ultrasound image 410 is registered or re-registered based on the fixed external image 420. Also, an initial state is assumed in which the ultrasound image 410 mismatches with the fixed external image 420 and thus needs to be rotated by a predetermined angle with respect to the x-axis, as shown in e1 of FIG. 13. Also, it is assumed that operation for matching the ultrasound image 410 with the fixed external image 420, as shown in e2 of FIG. 13, is performed.

In order to accurately match the ultrasound image 410 with the fixed external image 420, a user may move the ultrasound probe P on an object. The ultrasound image 410 output on the display unit 400 may be moved or rotated in correspondence to the movement of the ultrasound probe P. Then, the user may visually recognize a degree of tilting between the ultrasound image 410 and the external image 420 from the rotation information (for example, the images shown in FIGS. 9 to 11) of images displayed together with the ultrasound image 410 and the external image 420 on the display unit 400, thereby quickly and conveniently registering the ultrasound image 410 with the external image 420.

However, the embodiment of FIG. 13 is only an example for convenience of description, and the rotation information may be not necessarily displayed together with the ultrasound image 410 and the external image 420.

The above-description relates to a process of registering an ultrasound image with an external image to some degree, and then re-registering or more accurately re-registering the ultrasound image with the external image due to the generation of error, however, the technical concept of the present disclosure may be also applied to a process of registering an ultrasound image with an external image.

The ultrasound imaging apparatus of accurately and quickly registering an ultrasound image with an external image registered with the ultrasound image, based on various interfaces displayed on the display unit, using the ultrasound probe upon re-registeration, when the ultrasound image displayed on the display unit 400 has not accurately registered with the external image displayed on the display unit 400, and the method of controlling the ultrasound imaging apparatus have been described above.

According to the ultrasound imaging apparatus and the method of controlling the ultrasound imaging apparatus, as described above, it is possible to simply and quickly match an ultrasound image with an external image registered with the ultrasound image using the ultrasound probe.

More specifically, by fixing one of an ultrasound image and an external image and changing the other one in correspondence to movement of the ultrasound probe, it is possible to conveniently and quickly compare the ultrasound image to the external image based on reference lines displayed on the display unit.

Also, according to the ultrasound imaging apparatus and the method of controlling the ultrasound imaging apparatus, as described above, it is possible to conveniently and quickly re-register an ultrasound image with an external image using the ultrasound probe, without having to use a separate device such as a trackball or a mouse, while more accurately and precisely re-registering the ultrasound image with the external image.

Although the present disclosure has been described based on the limited embodiments and drawings, various corrections and modifications from the above description can be made by one of ordinary skill in the art. For example, although the above-described techniques are performed in a different order from that of the above-described method, and/or the above-described components, such as system, structure, apparatus, and circuit, are coupled or combined in a different form from that of the above-described method, or replaced or substituted with other components or equivalents, proper results can be achieved. Therefore, the scope of claims which will be described below may cover other implementations, embodiments, and equivalents of the claims.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasound imaging apparatus comprising:
   a display unit configured to display an ultrasound image and an external image such that a first reference line overlaps the ultrasound image and a second reference line overlaps the external image;
   an ultrasound probe configured to receive a command for moving or rotating at least one image of the ultrasound image or the external image based on a predetermined reference coordinate system; and
   a controller configured to determine whether the ultrasound image matches with the external image according to manipulation of the ultrasound probe, and to control the display unit to synthesize the ultrasound image with the external image and to display the ultrasound image and the external image, when determining that the ultrasound image matches with the external image,
   wherein, when a command for selecting a first reference point of the ultrasound image is input by a user, the controller fixes the ultrasound image including the first reference point regardless of movement of the ultrasound probe, and controls the display unit to change the external image in correspondence to the movement of the ultrasound probe,
   wherein the controller determines whether the fixed ultrasound image matches with the external image changing in correspondence to the movement of the ultrasound probe adjusted by the user, based on an intersection of the first reference line displayed on the ultrasound image and an intersection of the second reference line displayed on the external image, and controls the display unit to synchronize the ultrasound image with the external image and to display the ultrasound image and the external image, when determining that the ultrasound image matches with the external image, and
   wherein the first reference line includes coordinate information of the ultrasound image, and the second reference line includes coordinate information of the external image.

2. The ultrasound imaging apparatus according to claim 1, wherein, when a command for selecting a second reference point of the external image is input by the user, the controller fixes the external image including the second reference point, and controls the display unit to change the ultrasound image in correspondence to the movement of the ultrasound probe.

3. The ultrasound imaging apparatus according to claim 2, wherein the controller determines whether the fixed external image matches with the ultrasound image changing in correspondence to the movement of the ultrasound probe adjusted by the user, based on the first reference line displayed on the ultrasound image and the second reference line displayed on the external image, and controls the display unit to synchronize the ultrasound image with the external image and to display the ultrasound image and the external image, when determining that the external image matches with the ultrasound image.

4. The ultrasound imaging apparatus according to claim 1, wherein the display unit displays the first reference line and the second reference line in the form of grids including at least one line of a straight line or a curved line.

5. The ultrasound imaging apparatus according to claim 4, wherein the display unit further displays at least one of a character, a symbol, a numeral, or a figure around the first reference line and the second reference line, or at the intersection of the first reference line and the second reference line.

6. The ultrasound imaging apparatus according to claim 1, wherein the first reference line and the second reference line are displayed with the same color or with different colors according to a brightness of the entire or a part of the ultrasound image or a brightness of the entire or a part of the external image.

7. The ultrasound imaging apparatus according to claim 1, wherein the controller registers the ultrasound image with the external image.

8. The ultrasound imaging apparatus according to claim 7, wherein the display unit displays the ultrasound image and the external image registered with the ultrasound image.

9. The ultrasound imaging apparatus according to claim 1, wherein the display unit displays the first reference point of the ultrasound image or the second reference point of the external image, as at least one of a character, a symbol, a numeral, or a figure that is displayed in at least one position.

10. The ultrasound imaging apparatus according to claim 1, wherein the ultrasound probe comprises at least one sensor of a position sensor, an accelerometer, a magnetic sensor, or a gyro sensor.

11. The ultrasound imaging apparatus according to claim 10, wherein the ultrasound probe receives a command for moving or rotating at least one image of the ultrasound image or the external image based on the predetermined reference coordinate system, through the at least one sensor.

12. The ultrasound imaging apparatus according to claim 11, wherein the controller acquires information about a position and a direction of an object, using the ultrasound probe.

13. The ultrasound imaging apparatus according to claim 1, wherein the external image comprises at least one image of a re-sliced Computed Tomography (CT) image or a Magnetic Resonance Imaging (MRI), corresponding to the ultrasound image.

14. The ultrasound imaging apparatus according to claim 1, wherein the predetermined reference coordinate system includes an x-axis, a y-axis, and a z-axis.

15. A method of controlling an ultrasound imaging apparatus, comprising:

displaying an ultrasound image and an external image such that a first reference line overlaps the ultrasound image and a second reference line overlaps the external image;

receiving a command for moving or rotating at least one image of the ultrasound image or the external image based on a predetermined reference coordinate system; and determining whether the ultrasound image matches with the external image according to manipulation of the ultrasound probe, and controlling a display unit to synthesize the ultrasound image with the external image and to display the ultrasound image and the external image, when it is determined that the ultrasound image matches with the external image, wherein the controlling of the display unit comprises:

receiving a command for selecting a first reference point of the ultrasound image from a user;

fixing the ultrasound image including the first reference point regardless of movement of the ultrasound probe;

controlling the display unit to change the external image in correspondence to the movement of the ultrasound probe;

determining whether the fixed ultrasound image matches with the external image changing in correspondence to the movement of the ultrasound probe adjusted by the user, based on an intersection of the first reference line displayed on the ultrasound image and an intersection of the second reference line displayed on the external image; and controlling the display unit to synchronize the ultrasound image with the external image and to display the ultrasound image and the external image, when it is determined that the ultrasound image matches with the external image, and wherein the first reference line includes coordinate information of the ultrasound image, and the second reference line includes coordinate information of the external image.

16. The method according to claim 15, wherein the controlling of the display unit further comprises:

receiving a command for selecting a second reference point of the external image from the user;

fixing the external image including the second reference point; and controlling the display unit to change the ultrasound image in correspondence to the movement of the ultrasound probe.

17. The method according to claim 16, wherein the controlling of the display unit comprises:

determining whether the fixed external image matches with the ultrasound image changing in correspondence to the movement of the ultrasound probe adjusted by the user, based on the first reference line displayed on the ultrasound image and the second reference line displayed on the external image; and controlling the display unit to synchronize the ultrasound image with the external image and to display the ultrasound image and the external image, when it is determined that the external image matches with the ultrasound image.

18. The method according to claim 15, wherein the displaying of the ultrasound image and the external image comprises displaying the first reference line and the second reference line in the form of grids including at least one line of a straight line or a curved line.

19. The method according to claim 15, wherein the displaying of the ultrasound image and the external image comprises further displaying at least one of a character, a symbol, a numeral, or a figure around the first reference line and the second reference line, or at the intersection of the first reference line and the second reference line.

20. The method according to claim 15, wherein the first reference line and the second reference line are displayed with the same color or with different colors according to a brightness of the entire or a part of the ultrasound image or a brightness of the entire or a part of the external image.

21. The method according to claim 15, wherein the controlling of the display unit comprises registering the ultrasound image with the external image.

22. The method according to claim 21, wherein the displaying of the ultrasound image and the external image comprises displaying the ultrasound image and the external image registered with the ultrasound image.

23. The method according to claim 15, wherein the displaying of the ultrasound image and the external image comprises displaying the first reference point of the ultrasound image or the second reference point of the external image, as at least one of a character, a symbol, a numeral, or a figure that is displayed in at least one position.

24. The method according to claim 15, wherein the ultrasound probe comprises at least one sensor of a position sensor, an accelerometer, a magnetic sensor, or a gyro sensor.

25. The method according to claim 24, wherein the ultrasound probe receives a command for moving or rotating at least one image of the ultrasound image or the external image based on the predetermined reference coordinate system, through the at least one sensor.

26. The method according to claim 25, wherein the controlling of the display unit comprises acquiring information about a position and a direction of an object, using the ultrasound probe.

27. The method according to claim 15, wherein the external image comprises at least one image of a re-sliced Computed Tomography (CT) image or a Magnetic Resonance Imaging (MRI), corresponding to the ultrasound image.

28. The method according to claim 15, wherein the predetermined reference coordinate system includes an x-axis, a y-axis, and a z-axis.

* * * * *